(12) United States Patent
Huang

(10) Patent No.: US 7,740,746 B2
(45) Date of Patent: *Jun. 22, 2010

(54) DISPOSABLE ELECTROCHEMICAL SENSOR STRIP

(75) Inventor: Chun-Mu Huang, Sanchung (TW)

(73) Assignee: Delta Electronics, Inc., Taoyuan (TW)

( * ) Notice: Subject to any disclaimer, the term of this patent is extended or adjusted under 35 U.S.C. 154(b) by 861 days.

This patent is subject to a terminal disclaimer.

(21) Appl. No.: 11/415,720

(22) Filed: May 2, 2006

(65) Prior Publication Data

US 2006/0196768 A1    Sep. 7, 2006

Related U.S. Application Data

(62) Division of application No. 10/462,904, filed on Jun. 17, 2003, now Pat. No. 7,063,776.

(51) Int. Cl.
*G01N 27/327* (2006.01)

(52) U.S. Cl. ............. 204/403.04; 204/400; 204/403.01; 204/403.02

(58) Field of Classification Search ............ 204/403.04, 204/403.01, 403.02
See application file for complete search history.

(56) References Cited

U.S. PATENT DOCUMENTS

| | | | |
|---|---|---|---|
| 3,878,830 A | 4/1975 | Bicher | |
| 4,115,230 A | 9/1978 | Beckman | |
| 4,871,439 A | 10/1989 | Enzer et al. | |
| 4,970,145 A | 11/1990 | Bennetto | |
| 5,078,854 A | 1/1992 | Burgess et al. | |
| 5,607,566 A * | 3/1997 | Brown et al. | 257/414 |
| 5,997,817 A | 12/1999 | Crismore et al. | |
| 6,103,033 A | 8/2000 | Say | |
| 6,695,958 B1 * | 2/2004 | Adam et al. | 204/403.01 |
| 7,063,776 B2 * | 6/2006 | Huang | 204/403.14 |

FOREIGN PATENT DOCUMENTS

| | | |
|---|---|---|
| EP | 1098000 | 5/2001 |
| EP | 1098000 A2 * | 5/2001 |
| WO | 02/099407 | 12/2002 |

OTHER PUBLICATIONS

Chen et al., Applied Biochem & Biotech, 36, 1992, pp. 221-226.

* cited by examiner

*Primary Examiner*—Harry D Wilkins, III
*Assistant Examiner*—Bryan D. Ripa
(74) *Attorney, Agent, or Firm*—Volpe and Koenig, P.C.

(57) ABSTRACT

A disposable electrochemical sensor strip is provided. The sensor strip includes an isolating sheet having at least a through hole, at least a conductive raw material mounted in the through hole, a metal film covered on the conductive raw material to form an electrode which comprises an electrode working surface for processing an electrode action, and an electrode connecting surface, at least a printed conductive film mounted on the isolating sheet and having a connecting terminal for being electrically connected to the electrode connecting surface, and a signal output terminal for outputting a measured signal produced by the electrode action.

13 Claims, 19 Drawing Sheets

DISPOSABLE ELECTROCHEMICAL SENSOR STRIP

CROSS REFERENCE TO RELATED APPLICATIONS

This application is a divisional application of U.S. patent application Ser. No. 10/462,904, filed Jun. 17, 2003 which is relevant to U.S. application Ser. Nos. 11/109,169 and 10/354,684, which are incorporated by reference as if fully set forth.

FIELD OF INVENTION

The present invention relates to a disposable electromechanical sensor strip, and more particular to a structure and manufacturing method of a sheet type strip which is suitable for examining an analyte in a fluid sample, for example, the concentration of glucose in human blood, and the concentration of a uric acid.

BACKGROUND

Generally, utilization of a noble metal as an electrode material for an electrochemical sensor can achieve a high stability and a high reproducibility of detection and is a well-known technique in the field of electrochemistry. But, in the sensor, the only demand of the noble metal is a surface of an electrode, and other surfaces of the noble metal are unnecessary. Especially, for a disposable strip, the noble metal surfaces rather than the electrode are all squandered. The main purpose of the present invention is to provide a structure and a manufacturing method of a low-price metal electrode in a disposable electrochemical sensor strip for significantly reducing the demand of the noble metal and further reducing the cost.

The metal electrode according to the present invention also can be applied in various metal-catalyzed electrodes (not only noble metals) with a direct catalysis, besides in a noble electrode without chemical interference. The disposable electrode and the sensor according to the present invention can be suitable for all kinds of electrochemical detection electrodes, biosensors, fluid biochemical sensor (e.g., sewage, insecticide concentration, and heavy metal sensor strips), domestic medical application (e.g., blood glucose, uric acid, and cholesterol sensor strip).

The principle of electrochemical sensor has been developed and applied in detecting all kinds of fluid, biochemical ingredients. An electrochemical sensor may have different configurations for conforming to different functions. Please refer to FIG. 1. FIG. 1 shows that a basic framework of an electrochemical detecting device 10 includes the following components:

1. A container 12 for containing a fluid sample to be an electrochemical measure region 13.

2. A chemical reagent 14 for chemically reacting with an analyte contained in the fluid sample 11 and generating an output signal with an electric parameter, wherein the electric parameter corresponds to a biochemical ingredient of the analyte contained in the fluid sample 11. For example, if the fluid sample 11 is human blood and the analyte is glucose, the chemical reagent 14 is basically a glucose oxidase and a complex thereof.

3. Plural testing electrodes, as shown in FIG. 1, a counter electrode 15, a working electrode 16, and a reference electrode 17, for transmitting a working voltage for an electrochemical reaction from an electrochemical meter 18 to the container 12 and again transmitting the electric parameter to the electrochemical meter 18 after the analyte contained in the fluid sample 11 undergoes an electrochemical reaction so that the electrochemical meter 18 can process a numerical analysis and then display the result thereon.

4. An electrochemical meter 18 for providing the working voltage (or current) needed by the electrochemical reaction and measuring the electric parameter (output voltage or current) produced by the electrochemical reaction to record, or process the numerical analysis and display the testing data.

Meanwhile, plural testing electrodes can only include the counter electrode and the working electrode or further include a reference electrode. Moreover, a detecting electrode could be included as a fourth electrode. The number of the plural testing electrodes is varied according to the requirement of the electrochemical reaction.

The electrodes of different functions are made of different materials. In the laboratory, the counter electrode 15 is made of any conductive material, however the lower the conductive resistance the better the effect, such as a copper, a silver, a nickel, a graphite, a carbon, a gold, a platinum or other conductive materials, or can be a conductive membrane electrode formed by printing a carbon paste or a silver paste. The most common structure of the reference electrode 17 is a modified electrode 171 produced by means of printing or electroplating an Ag/AgCl film. Because the electric potential of the Ag/AgCl film is quite stable, it is extensively used as the reference electrode.

The selection of the working electrode 16 is more complex and can be sorted as two types, one is an electron-transfer mediator modified working electrode and the other is a metal-catalyzed electrode. The electron-transfer mediator modified working electrode has a chemical reagent immobilized thereon, wherein the chemical reagent includes an enzyme (such as a glucose oxidase) and a redox mediator (such as a potassium ferricyanide which is extensively used in the glucose testing piece). The enzyme and the analyte will react with each other to produce a new chemical compound (such as $H_2O_2$), the electrons generated from the redox reaction between the mediator and $H_2O_2$ is utilized to produce an electric signal, and through the electrode, the electric parameter can be outputted. The main purpose of this kind of electrode is only simply a conductor and is not involved in chemical catalysis. However, the material of the electrode should be selected specifically to avoid a chemical reaction with the fluid sample 11 or the chemical reagent 14 thereby interfering with the result.

The electrode without the chemical interference should be made of an inert conductive material, which is generally a noble metal (such as a gold, a platinum, a palladium, or a rhodium), or a carbon containing material (such as a carbon based screen printing electrode or a graphite bar). Furthermore, because carbon and the noble metal have no chemical reactivity in a low temperature, the chemical interference would take place. However, because the noble metal is more expensive, the carbon made electrode is usually applied as the electron-transfer mediator modified working electrode.

As to the metal-catalyzed electrode, it is made of a material which will directly and electrochemically reacts with the chemical reagent, the analyte, or the derivatives thereof, and has an ability of direct catalysis or a function of a single selectivity for the analyte. Thus, the mediator is not needed to add to the chemical reagent. This kind of electrode, not like the electrode only needs to be made of a chemically inactive metal, is generally made of a material that must have an ability to catalyze the reaction. Therefore, the material thereof should not be limited to be a noble metal but matched with the analyte, such as a copper, a titanium, a nickel, a gold, a platinum, a palladium, or a rhodium . . . etc., (for example, a rhodium electrode has an excellent ability to directly catalyze $H_2O_2$).

The two types of metal electrodes described above both have a high cost of the material and the processes when being formed under conventional manufacturing methods. This is especially true regarding the noble metal. Consequently, although the noble metal has a better stability, it cannot be the mainstream of the disposable medical treatment testing in family. Nowadays, the biggest requirement of the biosensor is the medical treatment in family for a blood glucose, a uric acid or a cholesterol . . . etc. And, the electrode used by these biosensors mostly belongs to the electron-transfer mediator modified working electrode, and thus the disposable testing sheet of the biosensor can have the carbon base screen printing electrode printed thereon for reducing the cost, as described in U.S. Pat. No. 5,985,116, which is a typical example.

Please refer to FIG. 2 which shows the example described in U.S. Pat. No. 5,997,817. In this patent, two conductive metal tracks 201 and 202 both coated by a palladium are fixed on an insulative backing 203 with an identical size for being the metal electrode of the sensor. A working electrode 204 and a counter electrode 205, electrode leads 206 and 207, and signal output terminals 208 and 209 are all integrally formed by palladium. However, the positions do necessarily be formed by palladium are only two tiny sections of the working electrode 204 and the counter electrode 205, and the other portions can only be formed by materials having a conductive characteristic rather than noble metal-palladium.

Further refer to FIG. 3 in which shows the example described in EP 1 098 000 and is another manufacturing method for the metal electrode. In this patent, an insulation sheet 301 previously injection molded has positions of a pattern 302 surrounded by recesses and islands 306, an electrode lead 303, and output terminals 304 and 305. Then, metallic deposit proceeds to deposit a metal layer on the surface of plastic insulation sheet. Due to all the surface of the insulation sheet being covered by deposited metal, an additional process has to be proceeded for removal of metal layer on the islands and remaining the patterns, the electrode leads and the output terminals. Thus, this method has a high cost and is only suitable for the electrode only formed by one kind of metal.

According to the technical defects described above, for reducing the manufacturing cost of the metal electrode in the disposable sensor strip and overcoming the problem of wasting the noble metal, the applicant devoted himself to develop a "structure and manufacturing method of disposable electrochemical sensor strip" through a series of experiments, tests and researches. In addition to effectively solving the wasting problem of the noble metal in prior arts, the electrodes according to the present invention can be formed or modified in advance respectively in different electroplating containers in a great quantity, and then be assembled to an isolating sheet for reducing manufacturing time thereof.

Furthermore, in addition to be employed as the noble metal electrode requiring no chemical interference, the metal electrode according to the present invention can also be employed as the metal-catalyzed electrode which has a direct catalyzing function. And, the disposable electrode and the sensor according to the present invention can be applied to all kinds of electrochemical testing electrodes, biosensors, biochemical analyte sensors for fluid (e.g., testing strips for a sewage, a pesticide content, a heavy metal ingredient etc.), all kinds of domestically medical treatment testing strips (e.g., testing strips for a blood glucose, a uric acid, and a cholesterol).

SUMMARY

It is an object of the present invention to form a metal film on a conductive raw material for reducing the amount of noble metal applied in the metal electrode of a disposable sensor strip.

It is another object of the present invention to provide metal electrodes which can be formed and modified respectively in different electroplating containers in a great quantity in advance and then be assembled to an isolating sheet for reducing the manufacturing time thereof.

It is a further object of the present invention to provide a metal electrode which can be mounted in a through hole of an isolating sheet, wherein an area of the through hole is an area of a working surface of the metal electrode. Additionally, the accurate area of the through hole can be achieved easily from the massive productivity of relevant industrial methods, and a stable working surface of the metal electrode was acquired simultaneously. And, because the testing signal produced by the sensor is in proportion to the electrode area, the present invention can therefore substantially increase the accuracy of reproducibility of the electrochemical sensor.

It is an additional object of the present invention to employ a tenon on an isolating sheet for being fixed in a notch of a measuring device.

In accordance with an aspect of the present invention, a disposable electrochemical sensor strip includes an isolating sheet having at least a through hole, at least a conductive raw material mounted in the through hole, a metal film covering on the conductive raw material to form an electrode, which comprises an electrode working surface for processing an electrode action, and an electrode connecting surface, at least a printed conductive film mounted on the isolating sheet and having a connecting terminal for being electrically connected to the electrode connecting surface, and a signal output terminal for outputting a measured signal produced by the electrode action.

Preferably, the conductive raw material of the sensor strip is metallic so as to form a metallic electrode with the metal film.

Preferably, the conductive raw material has a material selected from a group consisting of a copper, a brass, an oxygen-free copper, a bronze, a phosphorized copper, a nickel silver copper and a beryllium copper.

Preferably, the sensor strip further includes a chemical reagent mounted on the electrode working surface for detecting an analyte through reacting with the analyte contained in a fluid sample so as to produce the measured signal which is then outputted through the signal output terminal.

Preferably, the electrode forms an electrode area in the through hole whose area is an area of the working surface for processing the electrode action and transmitting the measured signal.

Preferably, the printed conductive film is formed by printing a conductive paste on the isolating sheet so as to form the signal output terminal and the connecting terminal which is covered on the electrode connecting surface for electrically connecting with the electrode.

Preferably, the conductive paste is a conductive adhesive containing a material selected from a group consisting of a carbon, a silver, a copper, a nickel, an aluminum, a gold, a stainless steel and a combination mixture thereof.

Preferably, the strip further includes an insulating layer covered on the printed conductive film.

Preferably, the metal film is made of a material selected from a group consisting of gold, platinum, rhodium, ruthenium, iridium, silver, copper, nickel, titanium, chromium, iron and aluminum.

Preferably, the conductive raw material of the sensor strip is one of a carbon-including conductive plastic compound, a metal-including conductive plastic compound and a plastic material undergone with a conductive coating treatment.

Preferably, the conductive raw material of the sensor strip is modified by the metal film through a device selected from a group consisting of an electroplating device, an immersion plating device (chemical plating without electrifying), a metal deposition device, a printing device, a metal spraying device.

Preferably, the electroplating device holds an electroplating liquid containing a metal ion for coating the metal film on the conductive raw material.

Preferably, the conductive raw material is pre-modified with the metal film to form the electrode and then put in the through hole of the isolating sheet.

Preferably, the conductive raw material is pre-put in the through hole of the isolating sheet and then modified with the metal film through one of the electroplating device, the immersion plating device, the metal deposition device, the printing device, and the metal spraying device so as to form the electrode in the through hole.

Preferably, the metal film has a thickness ranged from 0.025~20 μm.

Preferably, the through hole and the conductive raw material respectively have a shape selected from a group consisting of a circular form, a rectangular figure and an annular shape and are engaged with each other.

Preferably, the isolating sheet has two through holes whose bottoms are joined together to form a U-shaped recess for engaging with the conductive raw material having a U-shaped cross section, the metal film is coated on the conductive raw material in the U-shaped recess for forming the electrode with the electrode working surface in one leg of the U-shaped recess and the electrode connecting surface in another leg of the U-shaped recess, which are at the same side with respect to the isolating piece, so that the electrode working surface, the electrode connecting surface and the printed conductive film are formed at the same side of the isolating sheet.

Preferably, the through hole is a first through hole, the conductive raw material is a first conductive raw material, the printed conductive film is a first printed conductive film, the metal film is a first metal film, and the electrode is a first electrode to serve as a working electrode.

Preferably, the sensor strip further includes a second conductive raw material mounted in a second through hole of the isolating sheet, a second metal film modified on the second conductive raw material to form a second electrode which comprises a second electrode working surface which serves as a counter electrode and a second electrode connecting surface, and a second printed conductive film mounted on the isolating sheet and having a second connecting terminal which is electrically connected with the second electrode connecting surface, and a second signal output terminal.

Preferably, the sensor strip further includes a third conductive raw material mounted in a third through hole of the isolating sheet, a third metal film modified on the third conductive raw material to form a third electrode which comprises a third electrode working surface which serves as a reference electrode and a third electrode connecting surface, and a third printed conductive film mounted on the isolating sheet and having a third connecting terminal which is electrically connected with the third electrode connecting surface, and a third signal output terminal.

Preferably, the third metal film is a silver metal film, which is immersion plated in a chemical solution, electroplated in a chemical solution or printed by an AgCl paste thereon through a printing device so that the silver metal film is modified into an Ag/AgCl reference electrode.

Preferably, the isolating sheet has a flowing recess located at an edge portion above the electrodes for providing a fluid sample a space to flow therein, the flowing recess has a fluid inlet located at a side of the isolating sheet, the fluid inlet, the flowing recess and the through holes are integrally formed, a covering layer is covered on the flowing recess of the isolating sheet for forming a capillary channel and a measuring section by cooperating with the fluid inlet and the flowing recess, and the flowing recess further comprises a capillary vent for forming the capillary channel by cooperating with the fluid inlet.

Preferably, the counter electrode and the working electrode form an electrode assembly and a space above the electrode assembly and under the measure region is provided to position therein a chemical reagent with an even thickness.

Preferably, the isolating sheet has a protruding spacer for raising the covering layer and separating the fluid sample from an adhesive on the covering layer.

Preferably, the counter electrode and the reference electrode are both printed electrodes on the isolating sheet, and the working electrode is a metal electrode which is modified from the conductive raw material and mounted in the through hole of the isolating sheet.

Preferably, the first electrode further comprises a modified layer immobilized thereon for forming a modified electrode.

In accordance with another aspect of the present invention, a disposable electrochemical sensor includes an isolating piece having at least a through hole, at least a conductive raw material mounted in the through hole, and a metal film coated on the conductive raw material for forming an electrode which comprises an electrode working surface for processing an electrode action, and a signal output terminal for outputting a measured signal.

Preferably, the sensor further includes a chemical reagent mounted on the electrode working surface for detecting an analyte in a fluid sample through reacting with the analyte so as to generate the measured signal which is then outputted through the signal output terminal.

Preferably, the isolating piece comprises a tenon which is fixed in a notch of a measuring device for placing the sensor on an exact testing position of the measuring device.

Preferably, the electrode comprises a signal output point for being connected to a signal connecting point of the measuring device, the isolating piece has a measuring recess located at a portion above the electrode for measuring a fluid sample, the measuring recess and the through hole are integrally formed, a meshed piece is mounted on the measuring recess for filtering an impurity in the fluid sample, the electrode and the chemical reagent are positioned under the meshed piece for forming a measuring region, a covering layer is covered on the meshed piece and adhered to the isolating piece for avoiding the meshed piece from escaping from the measuring recess, and the covering layer comprises an opening for dropping therein the fluid sample.

Preferably, the signal output terminal of the electrode has a rivet joint, the sensor strip further comprises a metallic thin strip mounted on the isolating piece and having an output terminal and an electrode connecting hole electrically retaining therein the rivet joint.

In accordance with a further aspect of the present invention, a disposable electrochemical sensor strip includes an isolating sheet having at least a recess, at least a metal electrode mounted in the recess and having an electrode working surface for processing an electrode action and a signal output terminal for outputting a measuring signal produced by the electrode action.

Preferably, the sensor strip further includes a metal film integrally formed with the metal electrode.

Preferably, the sensor strip further includes a conductive raw material which is integrally formed with the metal film and the metal electrode.

In accordance with an another aspect of the present invention, a disposable electrochemical sensor includes an isolating piece having at least a through hole, at least a metal electrode mounted in the through hole and having an electrode working surface and an electrode connecting surface so as to process an electrode action through the electrode action, and at least a printed conductive film mounted on the isolating piece and having a conductive connecting surface electrically contacting with the electrode connecting surface and a signal output terminal outputting a measured signal produced by the electrode action.

Preferably, the metal electrode is a copper electrode.

In accordance with an another aspect of the present invention, a disposable electrochemical sensor strip includes an isolating sheet having at least a through hole, and at least a metal electrode mounted in the through hole and having an electrode working surface for processing an electrode action and a signal output terminal for outputting a measured signal produced by the electrode action.

Preferably, the isolating sheet comprises a tenon fixed in a notch of a measuring device for positioning the strip on the measuring device.

In accordance with an additional aspect of the present invention, a method for manufacturing a disposable electrochemical sensor strip includes steps of providing an isolating piece having at least two recesses, preparing a conductive raw material assembly comprising a first and a second conductive raw material, forming a modified electrode through modifying the first conductive raw material, and forming the disposable electrochemical sensor strip through positioning the modified electrode and the second conductive raw material in the at least two recesses.

Preferably, the method further includes an electroplating procedure for modifying the first conductive raw material to form a metal film and obtain the modified electrode.

Preferably, the method further includes a printing procedure for forming at least a signal output terminal through printing at least a conductive film on the isolating piece to be electrically connected to an output signal of the electrode.

Preferably, the method further includes a chemical reagent immobilizing procedure for modifying the electrode to obtain an enzyme electrode.

The above objects and advantages of the present invention will become more readily apparent to those ordinarily skilled in the art after reviewing the following detailed descriptions, and accompanying drawings.

DETAILED DESCRIPTION OF THE PREFERRED EMBODIMENT(S)

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

Figure 4A:
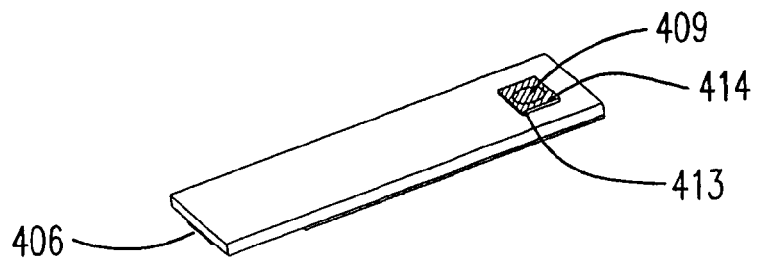
FIGS. 4(a)-(d) respectively, show a front view, a reverse view, a decomposed front view, and a schematic view of a conductive raw material modified by a metal film of the electrochemical sensor strip having one single electrode in a preferred embodiment according to the present invention.
Figure 4B:
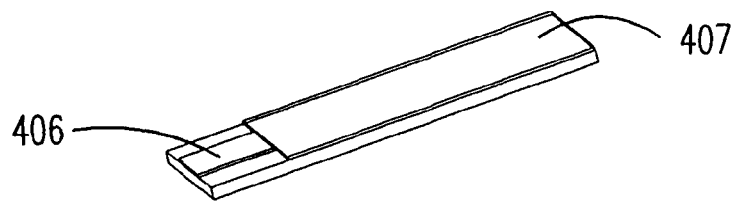
Figure 4C:
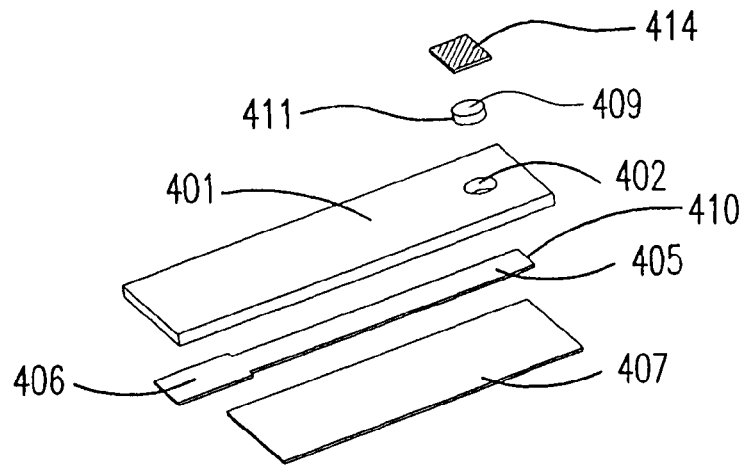
Figure 4D:
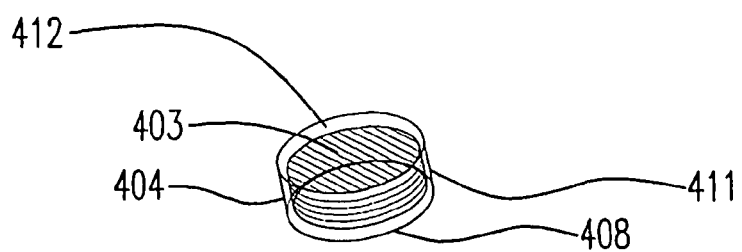

Please refer to FIGS. 4(a)-(c) illustrate the structure of a disposable electrochemical sensor strip having one single electrode according to the present invention. The strip includes an isolating sheet 401 (so called an insulating substrate) having a through hole 402. At least a conductive raw material 403 is mounted in the through hole 402 and is coated by a metal film 404 so as to form an electrode 411, wherein the electrode 411 includes an electrode working surface 409 and an electrode connecting surface 408. The electrode working surface 409 is employed to process an electrode action (namely, to be an electrode). Moreover, at least a printed conductive film 410 whose thickness is ranged from 1.0 µm to 20 µm having a connecting terminal 405 and a signal output terminal 406 is printed on the isolating sheet 401, wherein the connecting terminal 405 is electrically connected to the electrode connecting surface 408 and the signal output terminal 406 is employed to output a measured signal generated by the electrode action. Meanwhile, the conductive raw material 403 of the sensor strip can be made of a metal and then be coated by the metal film 404 to form a metal electrode 411.

Furthermore, the sensor strip includes a chemical reagent 414 mounted on the electrode working surface 409 of the metal electrode 411 so as to form an enzyme electrode 413 for examining an analyte in a fluid sample. The chemical reagent 414 reacts with the analyte to generate a measured signal that is then outputted through the signal output terminal 406. Moreover, the electrode 411 of the sensor strip will form an electrode area 412 in the through hole 402 for transmitting the measured signal. Namely, the isolating sheet 401 includes at least a through hole 402, the metal electrode 411 is formed by coating the metal film 404 on the conductive raw material 403 and tightly mounted in the through hole 402, the metal electrode 411 is peripherally mounted by the isolating sheet 401 for only revealing the electrode working surface 409 and the electrode connecting surface 408, and the electrode working surface is employed to process the electrode action.

Meanwhile, a conductive film 410 having a connecting terminal 405 and a signal output terminal 406 is printed on the isolating sheet 401, wherein the connecting terminal 405 is electrically connected to the electrode connecting surface 408 and the signal output terminal 406 is employed to output a measured signal generated by the electrode action. An insulating layer 407 is covered on a reverse side of the isolating sheet 401 so as to reveal only the signal output terminal 406 of the printed conductive film 410. Therefore, the conductive areas except the electrode working surface 409 can be isolated by the insulating layer 407 and will not contact with the fluid sample in order to avoid an examining accuracy from being influenced.

In this embodiment, the electrode material that really works is the metal film 404 made of a gold, a platinum, a palladium, a rhodium, a ruthenium, an iridium, a silver, a copper, a nickel, a titanium, a chromium, an iron and an aluminum. As to the conductive raw material 403, it should be made of a conductive material which can tightly combine with the metal film 404, so that the material can be any conductive metal, any carbon-including conductive plastic compound, any metal-including conductive plastic compound, or a plastic material undergone with a conductive coating treatment.

The methods for covering the metal film 404 on the conductive raw material 403 include an electroplating, an immersion plating, a metal deposition, a metal spraying. The conductive raw material 403 can be previously put in the through hole 402 and then be modified by the metal film 404, or, oppositely, the conductive raw material 403 can firstly be modified by the metal film 404 and then be put in the through hole 402. The best procedures of this embodiment are firstly plating a noble metal film 404 on the conductive raw material 403 through a mass plating method (namely putting many conductive raw materials 403 in one plating container) and then putting the coated conductive raw material into the through hole 402. The conductive raw material 403 can be made of a copper and an alloy thereof, such as a brass, an oxygen-free copper, a bronze, a phosphorized copper, a nickel silver copper and a beryllium copper. Because the copper and the alloy thereof are easily to form all kinds of electrode shapes and are conductive which is suitable for being modified by the metal film 404 through the plating process. The conductive raw material 403 can be made of the carbon-including conductive plastic compound by means of an injection-molding process. And, the carbon-including conductive plastic compound is conductive and suitable for being modified by the metal film through the plating process.

Nowadays, "plastic electroplating" has become a mature technology, which employs an injection-molding process to form the shape of the non-conductive plastic material 403 and further coats a conductive layer on the plastic material 403 for sequentially plating the metal film 404 thereon. Generally, a nickel layer will be previously coated on the plastic material, and then a needed metal film 404 is coated thereon.

The material of the printed conductive paste for forming the printed conductive film 410 can be a conductive adhesive containing a carbon, a silver, a copper, a nickel, an aluminum, a gold, a stainless steel and a combination mixture thereof, and the thickness of the printed film is ranged from 1.0 to 20.0 gm. The material of the isolating sheet 401 can adopt a polyvinyl chloride (PVC), a polypropylene (PP), a polycarbonate (PC), a polybutylene terephthalate (PBT), a polyethylene terephthalate (PET), a modified polyphenylene oxide (PPO) or an acrylonitrile butadiene styrene (ABS).

The thickness of the isolating sheet 401 is ranged from 0.2 mm to 3.0 mm. The conductive raw material 403 can be a circular form, a rectangular figure and an annular shape and has a thickness less than that of the isolating sheet 401 ranged from 0.00 mm to 0.15 mm, for example, the thickness of the isolating sheet is 0.60 mm, the through hole is circular with a diameter of 1.00 mm, and the raw material is a cylindrical copper plate with a thickness of 0.50 mm and a diameter of 1.02 mm. As the design described above, the diameter of the raw material is lightly larger than that of the through hole so as to ensure that they can tightly engage with each other. The metal film 404 covered on the electrode 411 can be a gold, a silver, a platinum, a rhodium, and a palladium, wherein when the metal film 404 of the electrode 411 is a silver, a silver chloride can be modified thereon for forming an Ag/AgCl reference electrode. Certainly, the conductive raw material 403 can be a copper and simultaneously the metal film 404 also can be a copper, namely the electrode 411 is a pure copper electrode.

The through hole 402 on the isolating sheet 401 can be formed through an injection-molding device, a punch press device, or a computerized drilling machine, and each of these mass producing methods can easily achieve an accurate dimension of the through hole over 99.5% reproducibility. If the electrode 411 is mounted in the through hole 402, it can firstly form the isolating sheet 401 having the through hole 402 through injection-molding, punch pressing, or the drilling and then put the electrode 411 in the through hole through a mechanical processing device so that they can tightly engage with each other, or it can put the electrode in a injection-molding device and inject a plastic material therein for forming the isolating sheet and simultaneously engaging the electrode in the through hole.

Figure 5A:
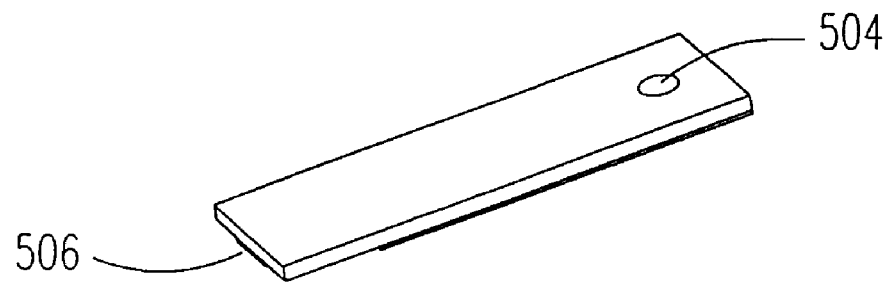
FIGS. 5(a)-(b) respectively, show a front view and a decomposed front view of the electrochemical sensor strip having one single electrode in a preferred embodiment according to the present invention.
Figure 5B:
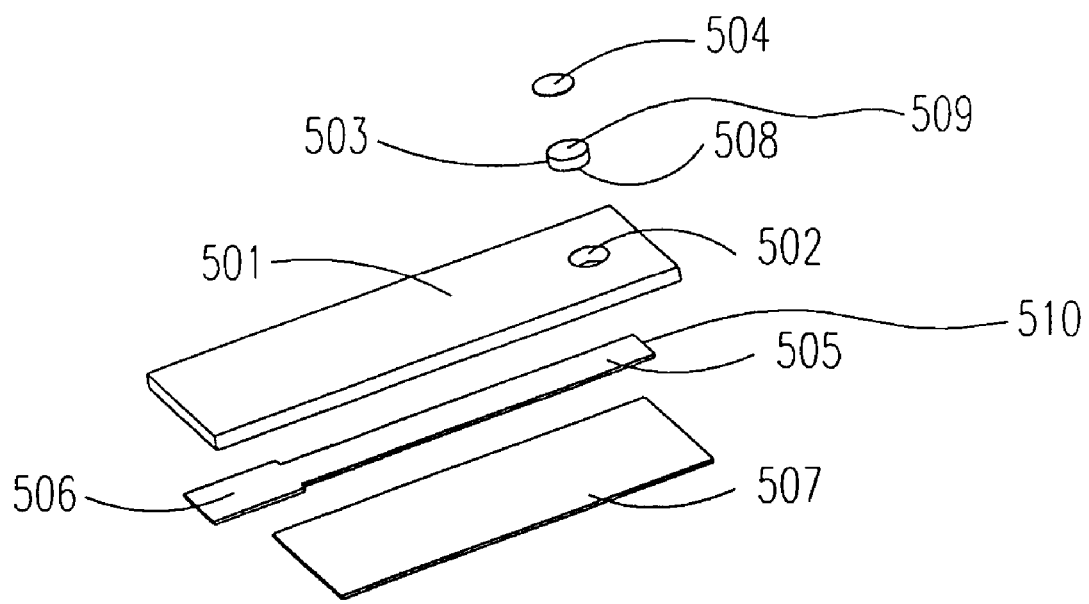

Please refer to FIGS. 5(a)-(b) which illustrate another sensor strip having one single electrode. The sensor strip includes an isolating sheet 501 having a through hole 502, and a conductive raw material 503 is put in the through hole 502 so that they can tightly engaged with each other, wherein the top 509 of the conductive raw material 503 is further coated by a metal film 504 so as to form a metal electrode (meanwhile, the conductive raw material 503 is a metal or a carbon-including conductive plastic compound). The metal electrode includes an electrode working surface 504 and an electrode connecting surface 508, wherein the electrode working surface is employed to process an electrode action. Moreover, a conductive film 510 having a connecting terminal 505 and a signal output terminal 506 is printed on the isolating sheet 501, wherein the connecting terminal 505 is electrically connected to the electrode connecting surface 508 and the signal output terminal 506 is employed to output a measured signal generated by the electrode action. As to number 507, it represents an insulating layer. The metal film 504 can be covered on the conductive raw material 503 by an electroplating, an immersion plating, a metal deposition, a metal spraying, or a metal printing.

Figure 6A:
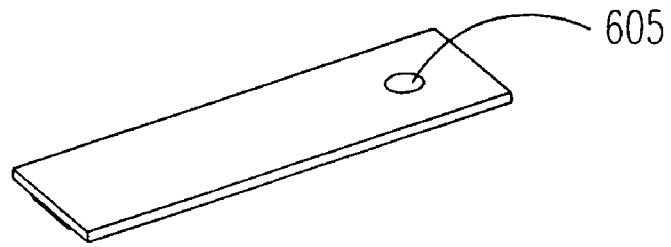
FIGS. 6(a)-(c) respectively, show a front view, a reverse view, and a decomposed front view of the electrochemical sensor strip having one single electrode in a preferred embodiment according to the present invention.
Figure 6B:
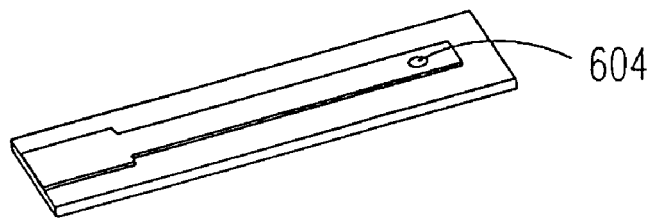
Figure 6C:
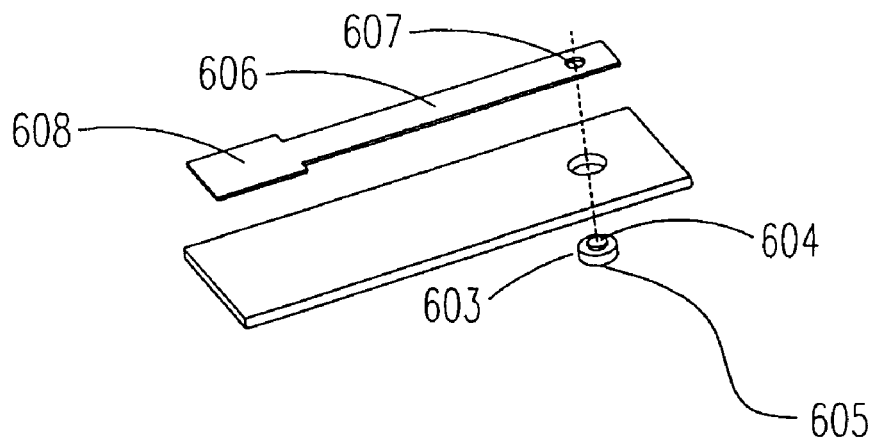

According to another aspect of the present invention, the printed conductive film 410 can be replaced. Please refer to FIGS. 6(a)-(c) which illustrate another sensor strip having one single electrode. In this embodiment, a metallic thin strip 606 is employed to replace the printed conductive film 410 in FIG. 4. The metal thin strip 606 has a signal output terminal 608 and a connecting hole 607, wherein the connecting hole 607 is electrically connected to a rivet joint 604 on a metal electrode 603 for outputting a measured signal generated by the electrode. As to number 605, it represents the electrode working surface. In this embodiment, the electrode can be a pure nickel electrode and also a pure iron electrode.

Figure 7A:
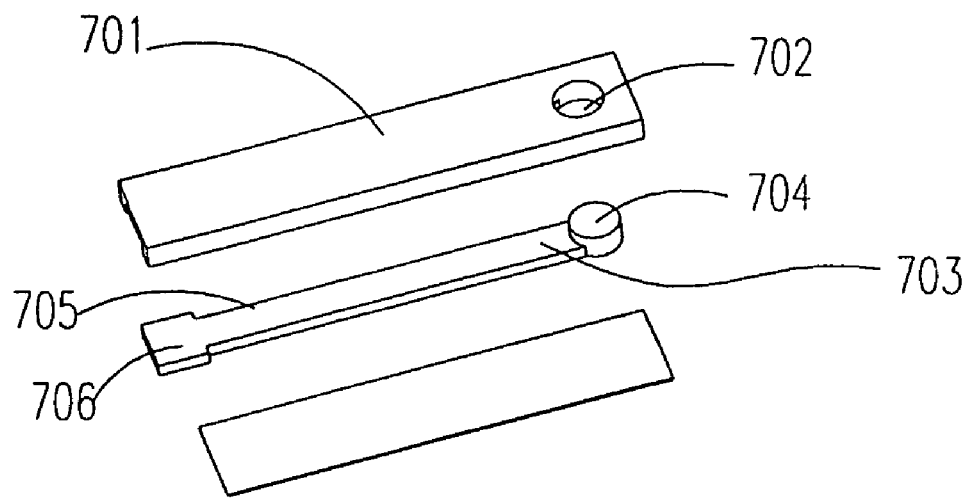
FIGS. 7(a)-(b) respectively, show a decomposed front view and a decomposed reverse view of the electrochemical sensor strip having one single electrode in a preferred embodiment according to the present invention.
Figure 7B:
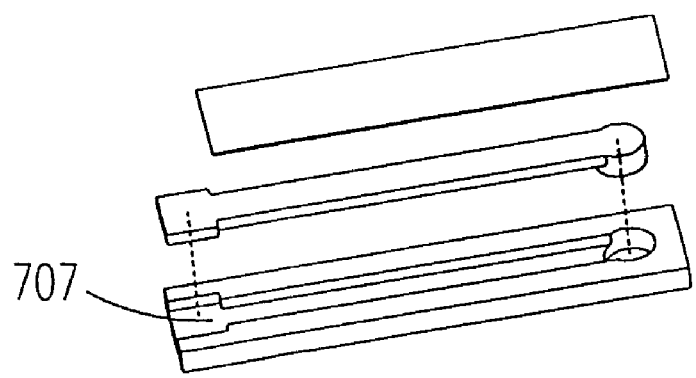

Furthermore, the conductive raw material 403 in FIG. 4 can be replaced by an integral metal so that an integral metal electrode is formed and the isolating sheet has to further form a recess for containing the metal strip, as shown in FIGS. 7(a)-(b). An integrally formed metal strip 703 is employed to replace the metallic thin strip 606 and the metal electrode 603 in FIG. 6. The metal strip 703 includes an electrode working surface 704, an electrode lead 705, and a signal output terminal 706, wherein the metal strip 703 can be integrally formed the electrode working surface 704, the electrode lead 705 and the signal output terminal 706 by an injection-molding or a punch pressing which is different from the printed conductive film 410 in FIG. 4. The isolating sheet 701 includes a through hole 702 and a recess 707 for mounting the metal strip 703 so as to engage with each other. Regarding to the process of covering a metal film on the metal strip 703 (not shown in FIG. 7), it can be achieved by firstly covering the metal film on the metal strip 703 and then putting thereof in the through hole 702, or previously putting the metal strip 703 in the through hole 702 of the isolating sheet 701 and then covering the metal film thereon.

Figure 8A:
FIGS. 8(a)-(b) respectively, show a structural front view and a decomposed front view of a modified electrode of a single electrode according to the present invention.
Figure 8B:
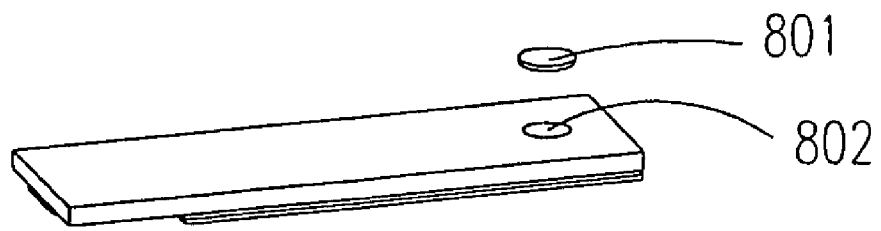

Please refer FIGS. 8(a)-(b) which illustrate a schematic view of a modified electrode. The metal electrodes in FIGS. 4-7 can be a working electrode or a counter electrode after properly selecting the conductive raw material and the metal film. For applying the electrochemical sensor, a modified layer 801 can be immobilized on the electrode 802 through a specific procedure so that the pure electrode 802 will be modified to be a modified electrode. For example, electrochemically immersing the metal electrode 802 which is coated by a silver film into a potassium chloride solution or printing the chlorine which will chemically react with the silver layer so as to form an Ag/AgCl reference electrode, or immobilizing or coating a chemical reagent 414 on the metal electrode 411 in FIG. 4 so as to form an enzyme electrode 413, wherein the chemical reagent can be a complex including at least a chemical material selected from a group consisting of an enzyme, a pH buffer, a surfactant/surface active agent, a redox mediator, a hydrophilic polymer compound, or a hydrophilic filtering mesh.

Figure 9:
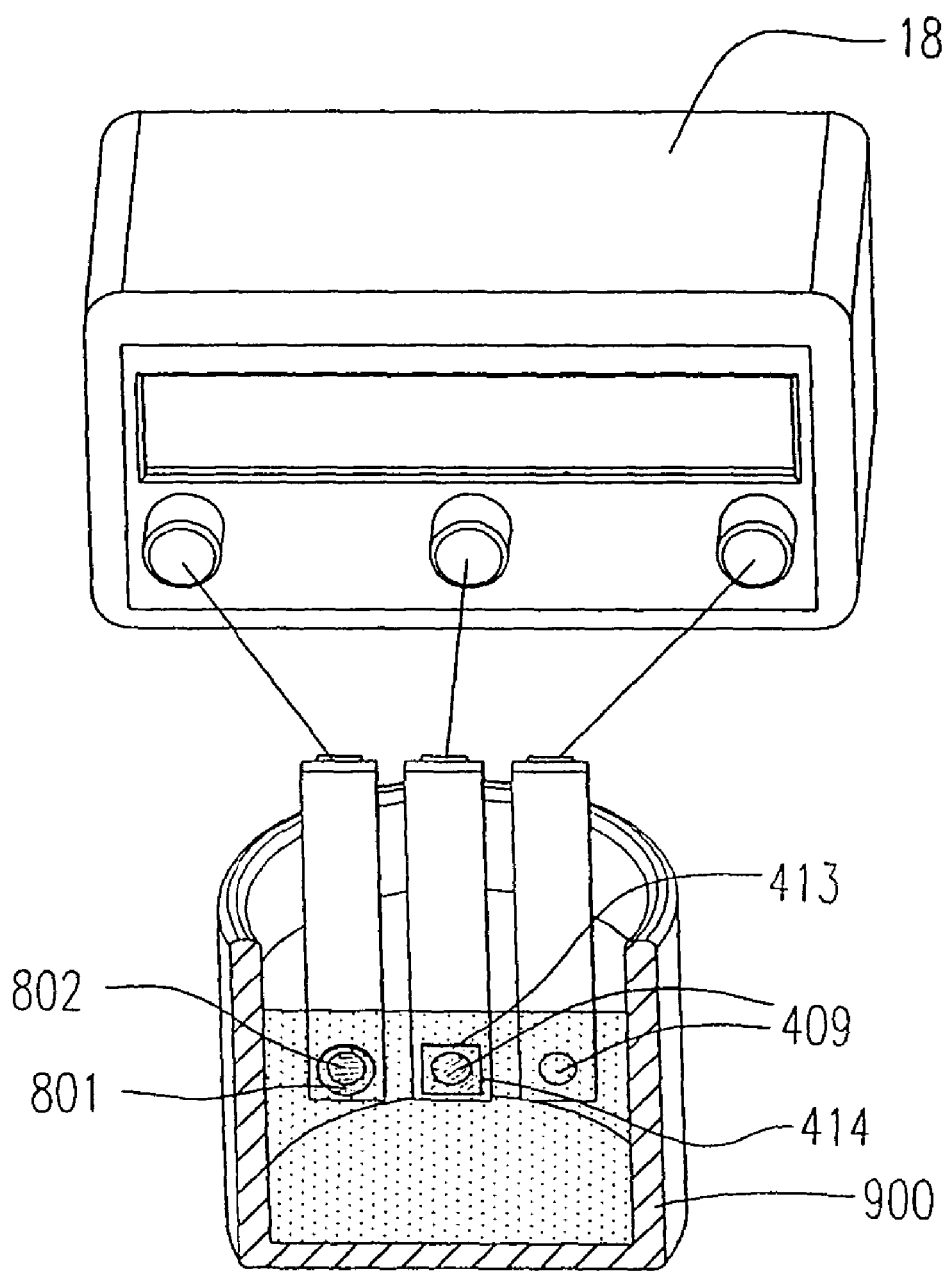
FIG. 9 shows a schematic view of an example employing a combination of the single electrode and modified electrode according to the present invention.

The chemical reagent 414 on the enzyme electrode 413 is employed to react with an analyte in a fluid sample so as to generate an electric measuring signal which will be outputted by the electrode 411 to a meter, such as the electrochemical measuring device 18 in FIG. 9, for being calculated to obtain the concentration of the analyte. When the chemical reagent 414 of the enzyme electrode 413 described above contains a redox mediator, the electrode will be an electro-transfer mediator modified working electrode. When the electrode 413 is modified by a proper metal film, the electrode will be a metal-catalyzed electrode, such as a platinum catalyzed electrode, a palladium catalyzed electrode, a gold catalyzed electrode, a rhodium catalyzed electrode, or a copper catalyzed electrode. When the enzyme contained in the chemical reagent 414 of the enzyme electrode 413 is glucose oxidase for examining human whole blood, the analyzing result of the fluid sample will be a blood glucose concentration of human blood. When the enzyme contained in the chemical reagent 414 is a uricase for testing human whole blood, the analyzing result of the fluid sample will be a uric acid concentration in human blood. When the enzyme contained in the chemical reagent 414 is a cholesterol oxidase for testing human whole blood, the analyzing result of the fluid sample will be a cholesterol concentration in human blood.

Figure 1:
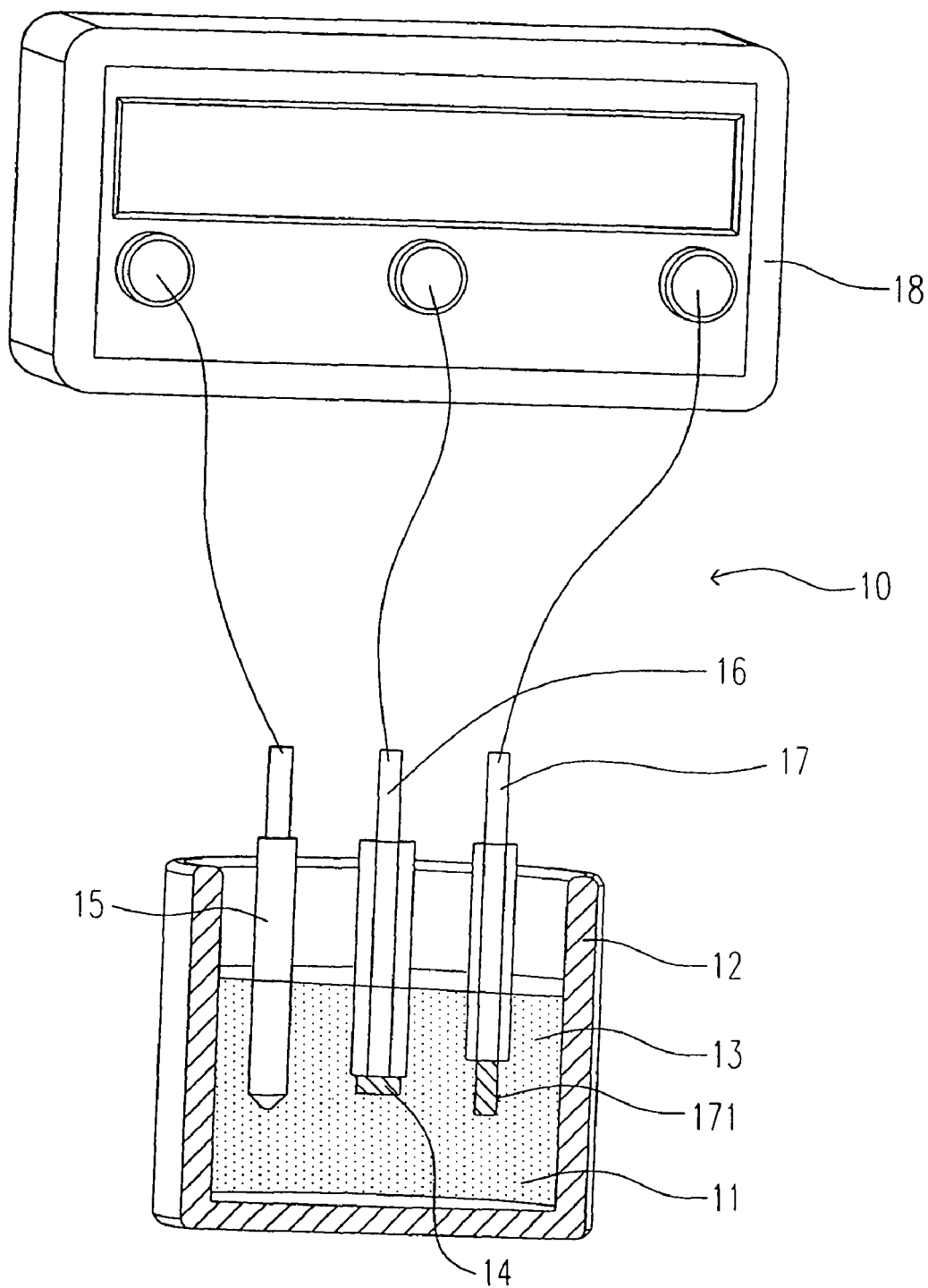
FIG. 1 shows a three-dimensional view of the basic electrochemical sensor equipment in the prior arts.
Figure 2:
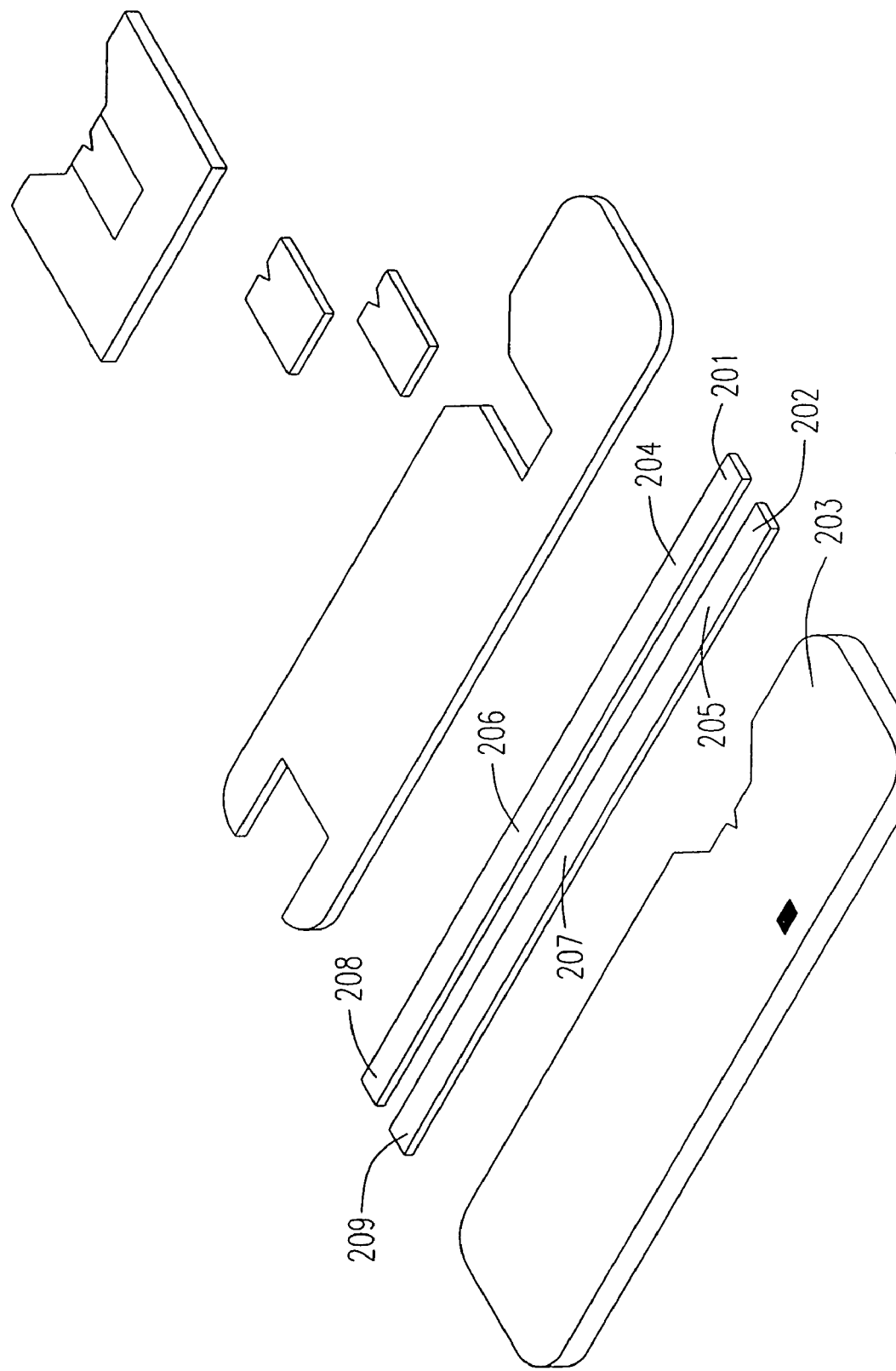
FIG. 2 shows a disposable metal electrode sensor in the prior arts.
Figure 3:
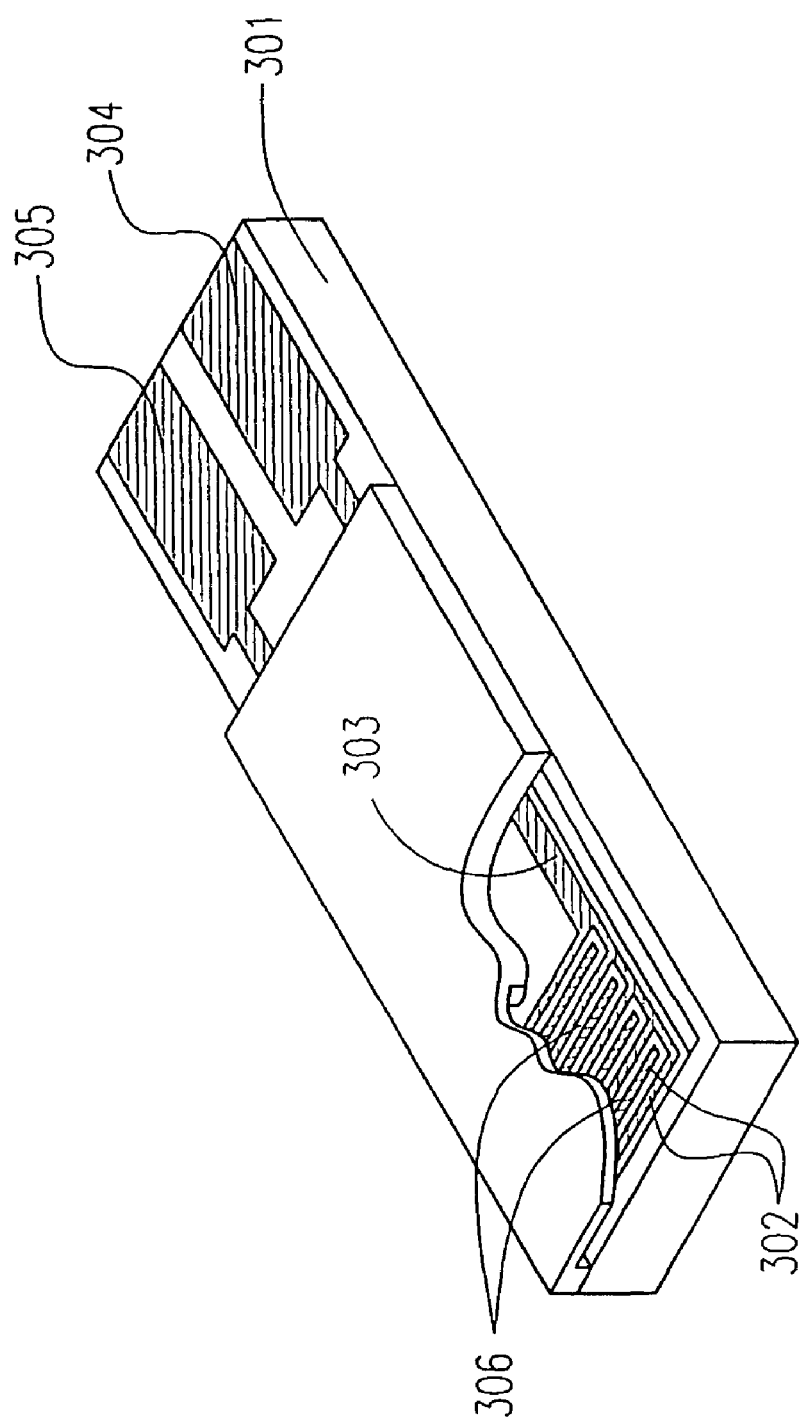
FIG. 3 shows a three-dimensional view of a disposable metal electrode sensor which is fabricated by a metal deposition in the prior arts.

Please refer FIG. 9 which illustrates an application of replacing the traditional electrode in FIG. 1 through three disposable testing strips according to the present invention. The conductive raw material of each electrode can be made of any conductive material and modified by a metal film to form a specific electrode. For example, employing three disposable sensor strips of a gold film counter electrode 409, an Ag/AgCl reference electrode formed by a silver film reference electrode 802 and an Ag/AgCl modified layer 801, and an enzyme working electrode 413 which is modified from a platinum film electrode for replacing the traditional electrode in FIG. 1.

Figure 10A:
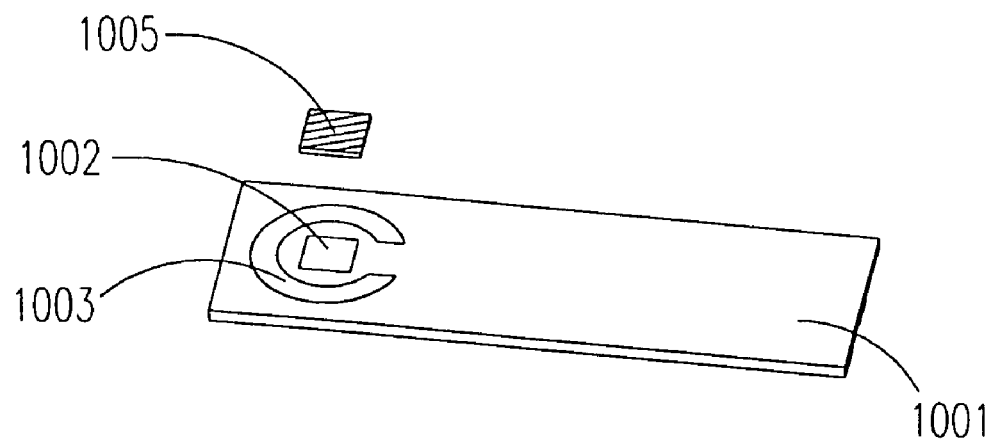
FIGS. 10(a)-(b) respectively, show a front view and a decomposed front view of the electrochemical sensor strip having two electrodes in a preferred embodiment according to the present invention.
Figure 10B:
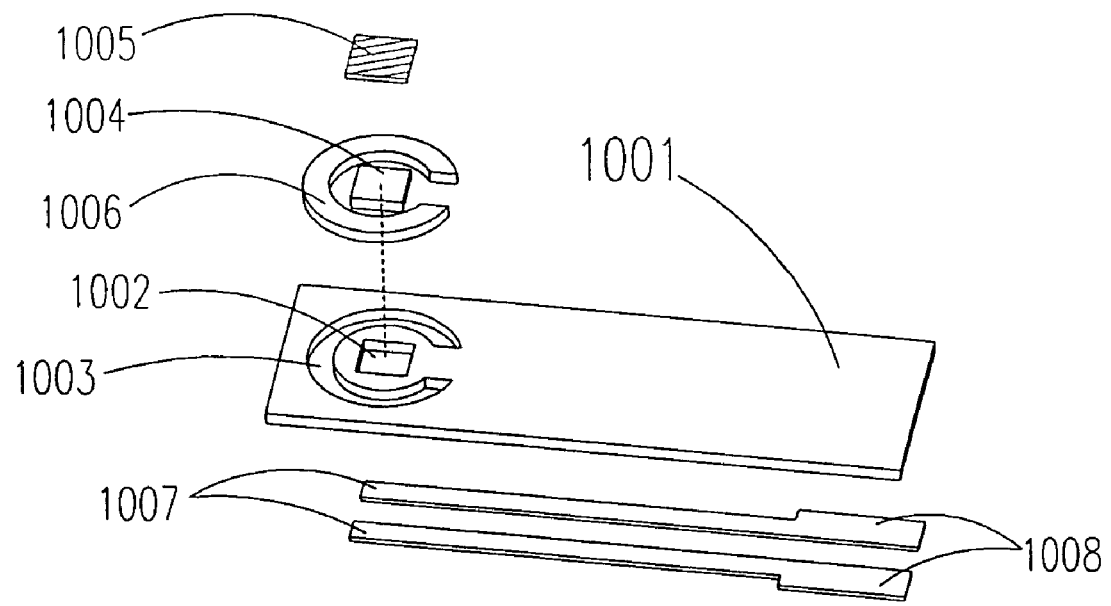

According to another aspect of the present invention, the recess 707 in FIG. 7 can be altered to receive only the through hole and not the metal conductive strip, as shown in FIGS. 10(a)-(b). FIGS. 10(a)-(b) illustrate a sensor strip having two electrodes in a preferable embodiment according to the present invention. The sensor strip includes an isolating sheet 1001 having a rectangular through hole 1002 and an annular through hole 1003 and a rectangular working electrode 1004 and an annular counter electrode 1006 are respectively mounted in the through holes 1002 and 1003 so as to engage with each other. Two connecting terminals 1007 of the conductive films are printed below the isolating sheet 1001 and two signal output terminals 1008 thereof are electrically connected to the metal electrodes 1004 and 1006 for outputting the measured signal generated by the electrode action. A chemical reagent 1005 is immobilized on the working electrode 1004 for reacting with an analyte in a fluid sample so as to produce an electric signal which is then outputted to a device, such as the electrochemical measuring device 18 in FIG. 1, through two electrode 1004, 1006, connecting terminals 1007 and output terminals 1008.

Figure 11:
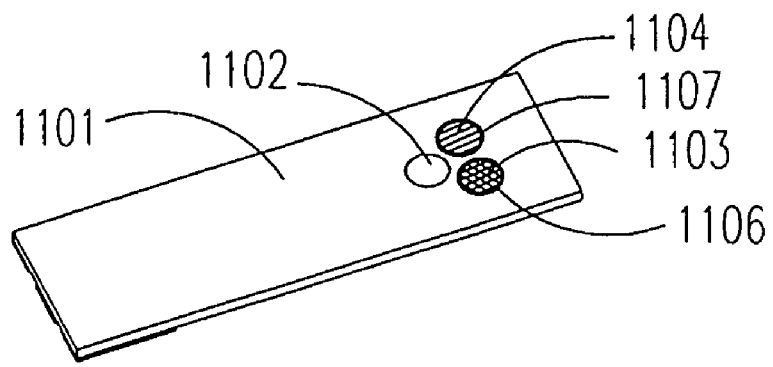
FIGS. 11(a)-(b) respectively, show a front view and a decomposed front view of the electrochemical sensor strip having three electrodes in a preferred embodiment according to the present invention.
Figure 11:
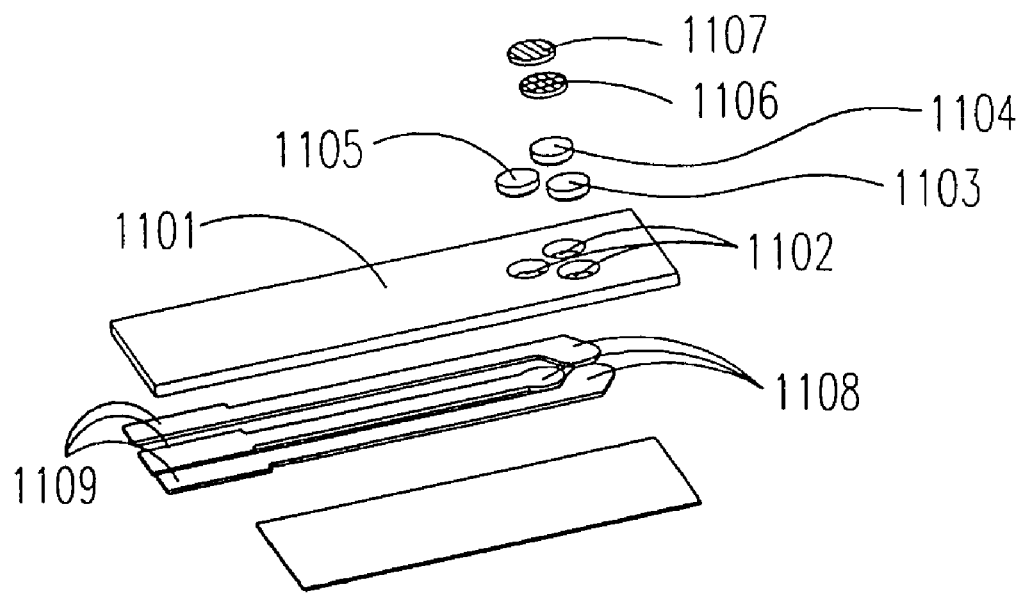

Please refer to FIGS. 11(*a*)-(*b*) which illustrate a sensor testing strip having three electrodes in a preferable embodiment according to the present invention. The sensor strip includes an isolating sheet 1101 having three though holes 1102, and a counter electrode 1105, a working electrode 1103 and a reference electrode 1104 are respectively mounted in three through holes 1102 so as to engage with each other. Three conductive films 1108 are printed below the isolating sheet 1101, and the three printed conductive films include signal output terminals 1109 which are respectively connected to the metal electrodes 1103, 1104 and 1105 for outputting the measured signal generated by the electrode action. An AgCl modified layer 1107 is coated on the reference electrode 1104 for modifying the electrode 1104 into an Ag/AgCl reference electrode. A chemical reagent 1106 is immobilized on the working electrode 1103 for reacting with the analyte in a fluid sample so as to generate an electric signal which will be outputted to a device 18 through the electrode 1103, and the output terminal 1109.

Figure 12:
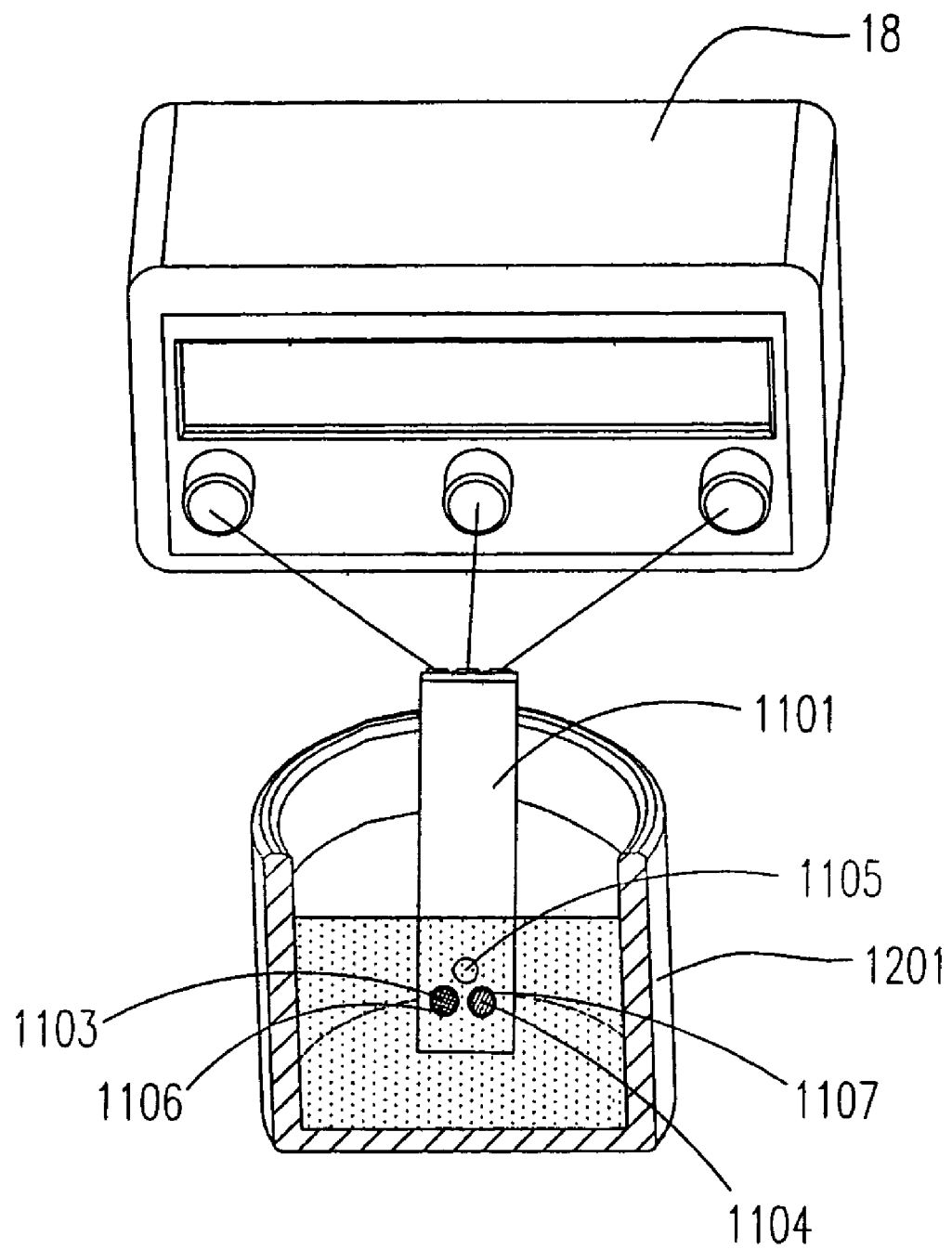
FIG. 12 shows a schematic view of an example employing the sensor strip having three electrodes according to the present invention.
Figure 13A:
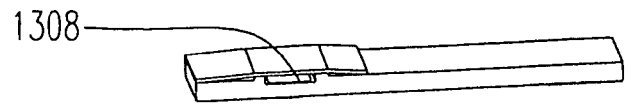
FIGS. 13(a)-(d) respectively show a front view, a reverse view, a decomposed front view, and a schematic view of a conductive raw material modified by a metal film of the electrochemical sensor strip having a capillarity channel (which is suitable for micro-liter fluid samples) in a preferred embodiment according to the present invention.
Figure 13B:
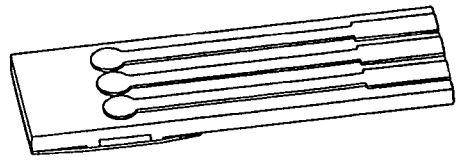
Figure 13C:
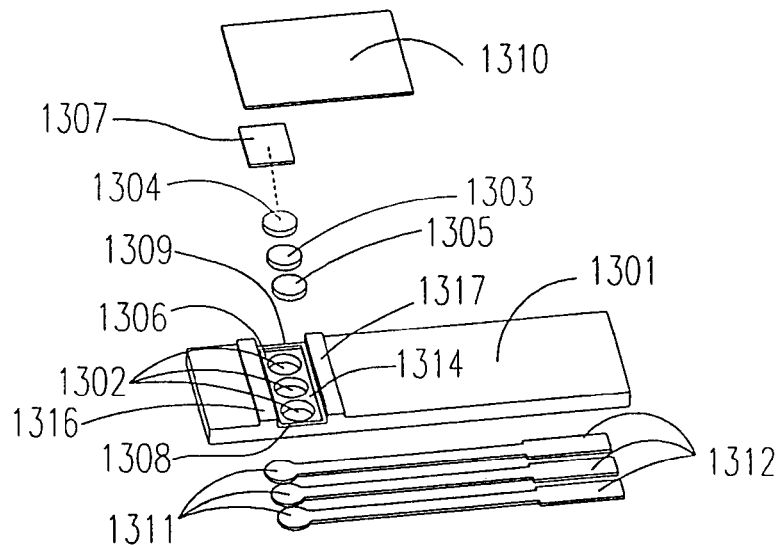
Figure 13D:
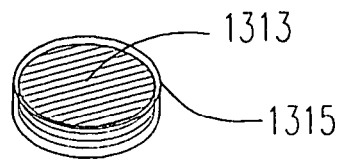

Please refer FIG. 12 which illustrates an application of replacing the traditional electrode in FIG. 1 with a disposable testing strip having three electrodes according to the embodiment in FIG. 11.

The embodiments shown in FIGS. 4-12 are suitable for testing medium to large amount samples. As to small amount samples (for example, the disposable sensor strip for human blood only uses blood of several μL), the sensor strip therefor generally additionally has a structure for absorbing the small amount sample in order to fully spread the sample over all electrodes. And, if the electrodes are not fully covered by the fluid sample, a testing error might be caused. Please refer to FIGS. 13(*a*)-(*c*) which illustrate an application employing a three electrode sensor strip having capillary channels according to the present invention. As shown in FIGS. 13(*a*)-(*c*), an adsorbing structure generally includes a capillary channel inlet 1308, a capillary channel 1314, and a capillary vent 1309, wherein the capillary channel 1314 is generally a measuring section for the fluid sample.

When the fluid sample attaches the capillary channel inlet 1308, because the capillarity, the fluid will be automatically adsorbed by the capillary channel 1314 until the measuring section is fully by the fluid. FIGS. 13-18 all are embodiments of sensor strips suitable for small amount samples. Firstly, FIG. 13 shows a three electrode sensor strip having a capillary channel for examining the small amount sample. The sensor strip includes an isolating sheet 1301 having a fluid measuring recess 1314 (namely the capillary channel 1314). The bottom of the fluid measuring recess 1314 is a chemical reagent placing recess 1306 for placing a chemical reagent 1307 so as to have a uniform distribution thereof. Three through holes 1302 are positioned under the placing recess 1306 for respectively receiving a working electrode 1303, a counter electrode 1305, and a reference electrode 1304.

The three electrodes 1303, 1304 and 1305 are engaged with the through holes 1302 and are respectively covered by a metal film 1315 (as shown in FIG. 13(*d*), to form a metal electrode 1303, 1304 and 1305. Each of the electrodes 1303, 1304 and 1305 includes an electrode working surface and an electrode connecting surface wherein the electrode connecting surface is utilized to process an electrode action. Meanwhile, three printed conductive films 1311 are positioned under the isolating sheet 1301 and each of which includes a connecting terminal and a signal output terminal 1312. The connecting terminal of each printed conductive film 1311 is respectively and electrically connected to the electrode connecting surface of each electrode so as to output a measured signal through the signal output terminal 1312. Moreover, the fluid measuring recess 1314 further includes a fluid inlet 1308 and the capillary vent 1309, and a covering layer 1310 is positioned on the recess 1314 so as to compose a completed capillary adsorbing structure. Furthermore, the isolating sheet 1301 has two protruding spacers 1316 and 1317 for raising the covering layer 1310 and separating the fluid sample from an adhesive on the covering layer 1310.

The chemical reagent 1307 is positioned on the top of three electrodes 1303, 1304 and 1305 for reacting with an analyte in the fluid sample so as to generate an electric signal which is then outputted to a device 18 through the electrodes 1303, 1304, 1305 and the signal output terminal 1312, wherein the electric signal is proportional to a concentration of the analyte and utilized to calculate a parameter of the analyte. The conductive raw material 1313 of each electrode 1303, 1304 and 1305 can be made of any conductive material. The metal film 1315 for covering the working electrode 1303 can be a gold, the metal film 1315 for covering the reference electrode 1304 can be a silver which can be coated by a silver chloride layer to form an Ag/AgCl reference electrode, and the metal film 1315 for covering the counter electrode 1305 can be a platinum.

Certainly, the metal film 1315 for covering the working electrode 1303 can be a rhodium, a palladium, a ruthenium and a copper, and when the metal film is a copper, the metal substrate 1313 can also be a copper, namely the electrode is integrally formed by a copper.

According to the embodiment described above, the present invention also provides a method for manufacturing a disposable electrochemical sensor strip. The method includes providing an isolating sheet 1301 having at least two recesses (through holes) 1302, preparing a conductive raw material assembly including a first and a second conductive raw material (namely the conductive raw material 1313), modifying the first conductive raw material to form a modified electrode 1315 (which can be electroplated by a platinum to be a working electrode or be electroplated by an Ag/AgCl layer to be reference electrode), and forming the disposable electrochemical sensor strip through positioning the modified electrode and the second conductive raw material in two recesses 1302. The method further includes an electroplating procedure for covering a metal film on the first conductive raw material to form the modified electrode 1315, and a step of immobilizing a chemical reagent for obtaining an enzyme electrode.

Figure 14:
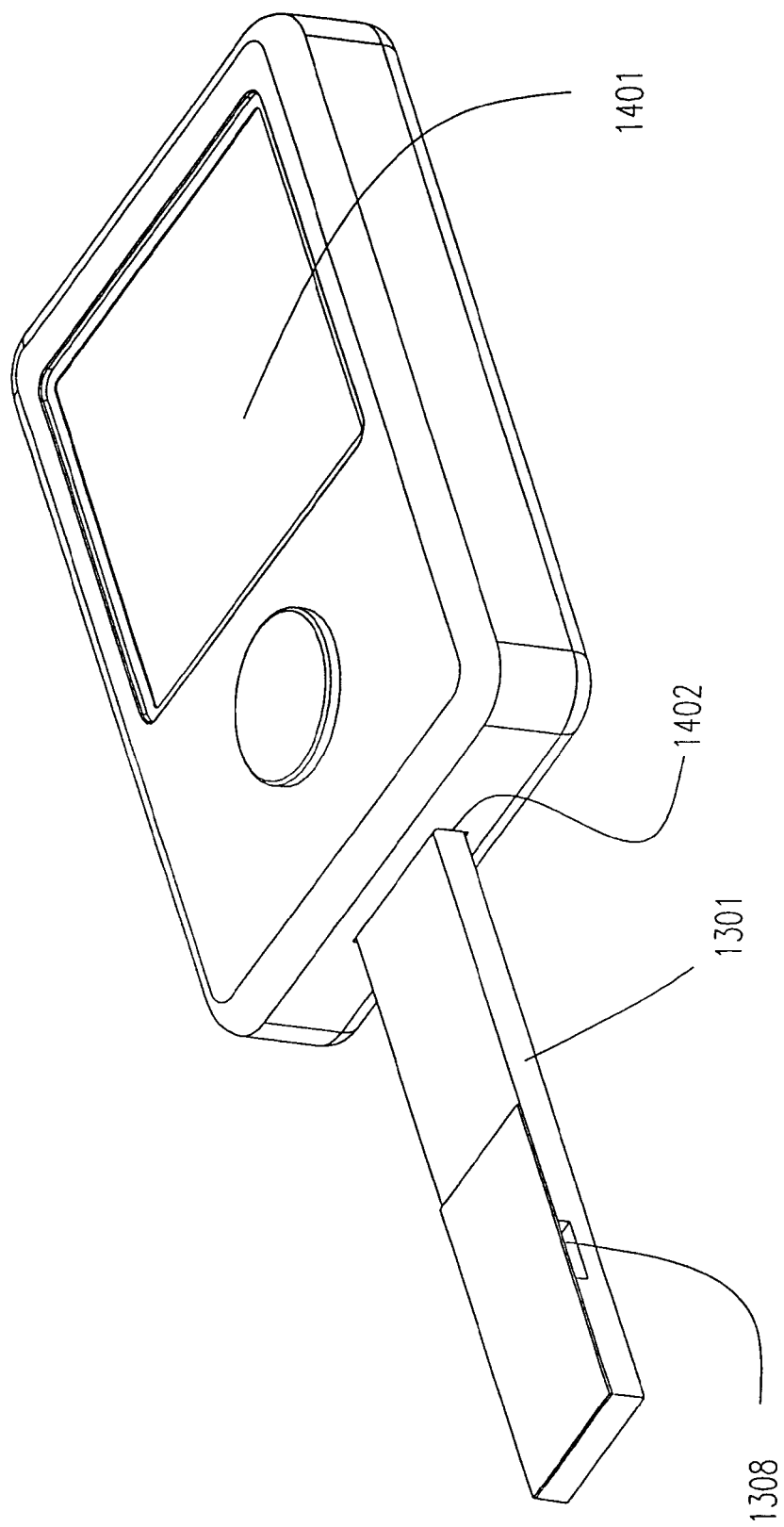
FIG. 14 shows a front schematic view of an example employing a combination of the sensor strip and a measuring device according to the present invention.

Please refer to FIG. 14 which illustrates a combination of embodiments of the sensor strips in FIGS. 13-17 and a device. An electrochemical device 1401 includes an inlet 1402 which is employed to guide an electrochemical sensor strip 1301 thereinto and the fluid sample will be adsorbed by the capillary channel inlet 1308. The device 1401 provides a sufficient working potential needed by an electrochemical reaction to each electrode and receives the measured signal outputted by the electrode and displays an information after calculating the measured signal.

Figure 15A:
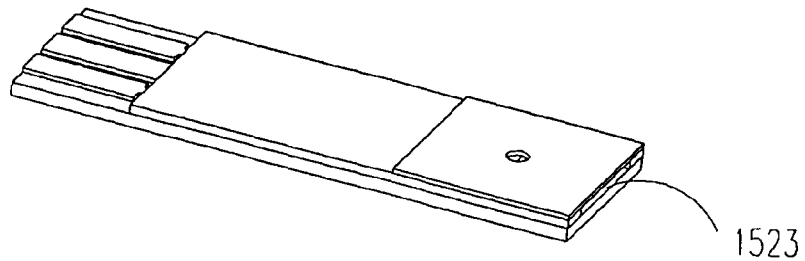
FIGS. 15(a)-(c) respectively show a front view, a reverse view, and a decomposed front view of the electrochemical sensor strip having three electrodes in another preferred embodiment according to the present invention.
Figure 15B:
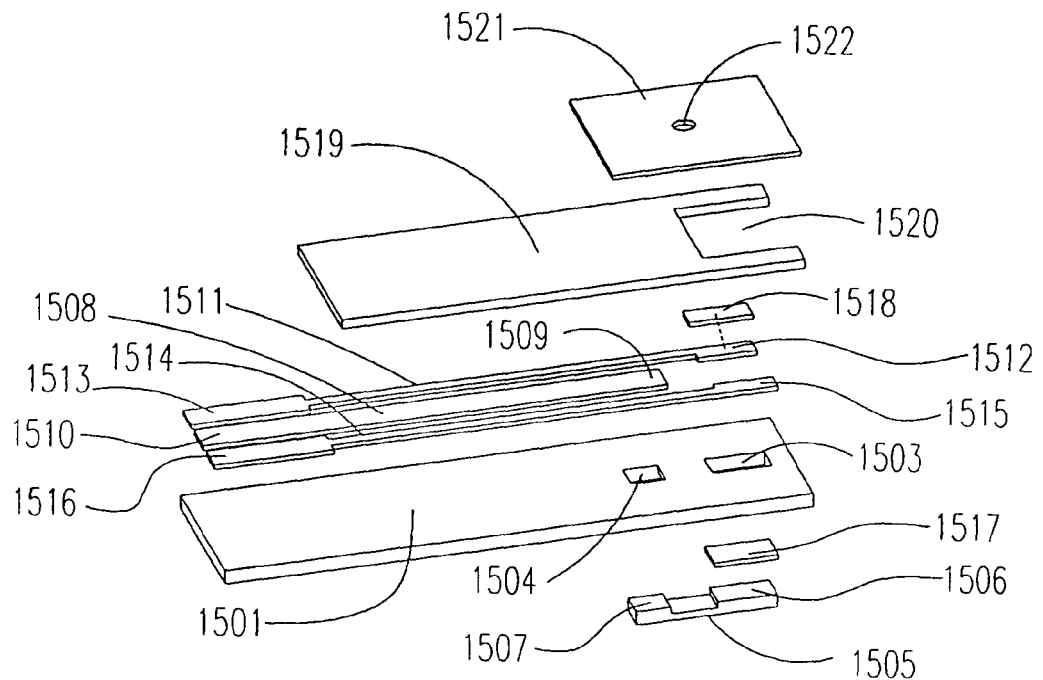
Figure 15C:
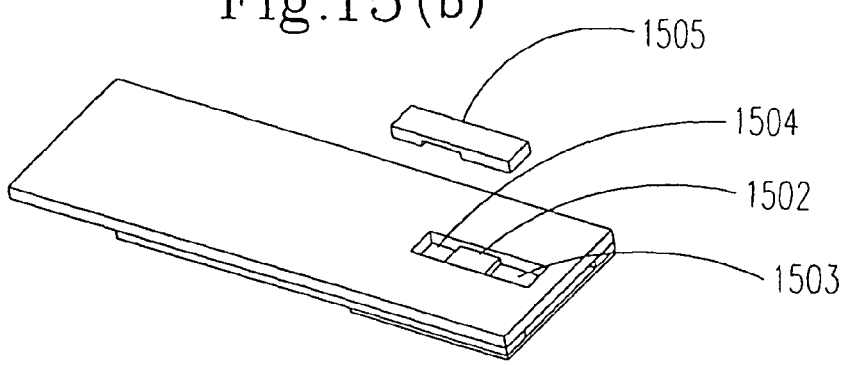

Please refer to FIGS. 15(a)-(c) which illustrate another embodiment of the present invention, applying a three electrode sensor strip having the capillary channel. This sensor strip includes an isolating sheet 1501 having a first through hole 1503 for an electrode working surface and a second through hole 1504 for an electrode connecting surface, wherein the bottoms of the first and the second through holes are joined together to form a U-shaped recess 1502 for engaging with an electrode having a U-shaped cross section. The U-shaped electrode 1505 includes an electrode working surface 1506 and an electrode connecting surface 1507, both of which are located at the same side with respect to the isolating sheet 1501. The electrode working surface 1506 is utilized to process an electrode action.

Furthermore, a first printed conductive film 1508, a second printed conductive film 1514, and a third printed conductive film 1511 are simultaneously printed on the isolating sheet 1501. The first printed conductive film 1508 having a connecting terminal 1509 and a working electrode output terminal 1510 is printed on the isolating sheet 1501 and covered on the electrode connecting surface 1507, wherein the connecting terminal 1509 is electrically connected to the electrode connecting surface 1507 for outputting the measured signal to the output terminal 1510. The second printed conductive film 1514 having a counter electrode output terminal 1516 and a second electrode terminal 1515 to be a counter electrode 1515, and the third printed conductive film 1511 having a reference electrode output terminal 1513 and a third electrode terminal 1512 to be a reference electrode 1512, wherein the reference electrode 1512 can be modified by a silver chloride layer 1518 to form an Ag/AgCl reference electrode.

Meanwhile, an insulating layer 1519 having a C-shaped opening 1520 is covered on the top of three conductive strips 1508, 1511, and 1514 except the electrode working surface 1506 and the electrode output terminal 1510. Then, a covering layer 1521 having a capillary vent 1522 thereon is covered on the C-shaped opening 1520 for forming a completed capillary adsorbing structure. Because of the cooperation between the U-shaped recess 1502 and the U-shaped electrode 1505 in this structure, the first conductive film 1508 for connecting the working electrode 1505 can be printed on the isolating sheet 1501 together with the second conductive film 1514 (with the counter electrode 1515) and the third conductive film 1511 (with the reference electrode 1512) at the same time. Therefore, one printing procedure can be abridged.

Besides, a chemical reagent 1517 is positioned on the top of the working electrode 1505 for reacting with an analyte in a fluid sample so as to generate an electric signal which is then outputted to the working electrode output terminal 1510 through the electrode 1505. Additionally, three printed conductive films 1508, 1511 and 1514 can be made of a carbon-including conductive paste or a silver paste. As to number 1523, it represents a fluid inlet.

In the embodiment described above, the working electrode 1505 is covered by the metal film to form a working electrode having a good performance, and the electrode working surface 1506 formed in the first through hole 1503 can be exactly obtained so as to significantly increase the qualitative reproducibility of the sensor. Regarding to the counter electrode 1515 and the reference electrode 1512, because the material and working surface thereof do not need to be as exact as the working electrode, they can be formed by the traditional printing method thereby, reducing the cost.

Figure 16A:
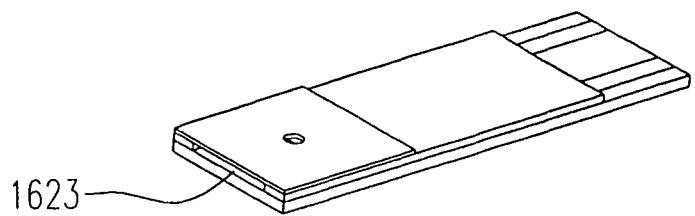
FIGS. 16(a)-(c) respectively show a front view, a reverse view, and a decomposed front view of the electrochemical sensor strip having three electrodes in further another preferred embodiment according to the present invention.
Figure 16B:
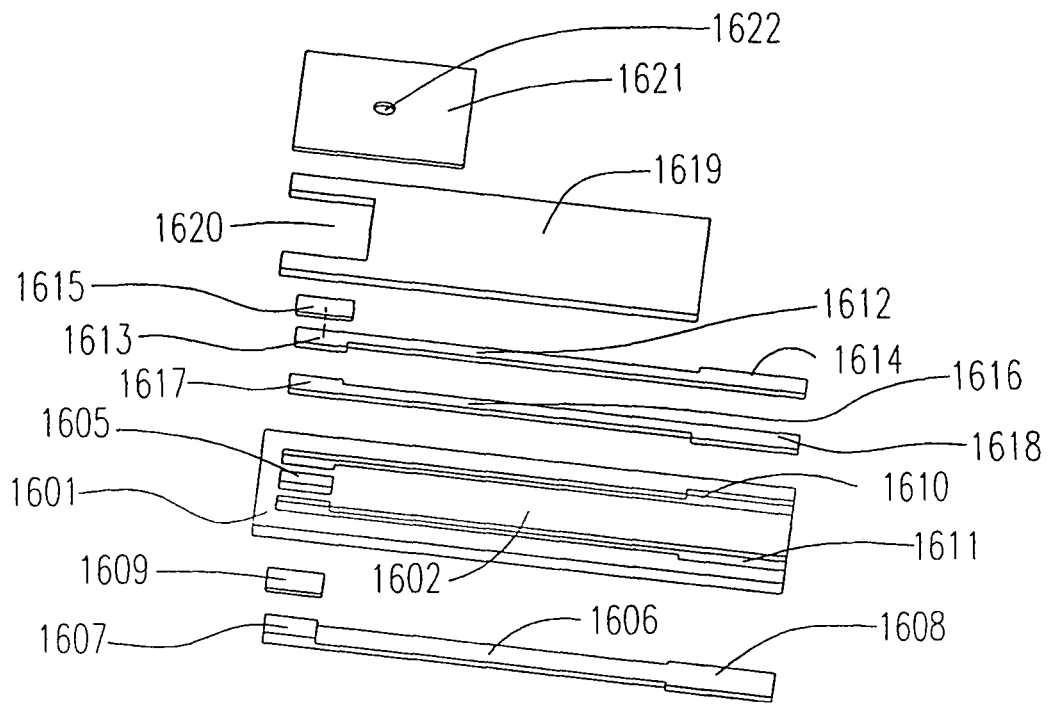
Figure 16C:
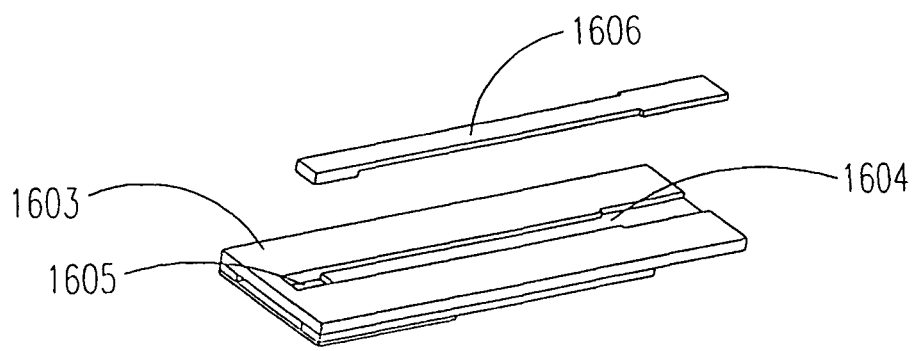

Please refer to FIGS. 16(a)-(c) which illustrate further, another embodiment of a three electrode sensor strip having the capillary channel according to the present invention. This embodiment is actually an alternation of the embodiment in FIG. 10 wherein the printed conductive film 1006 by an integrally formed conductive strip. In this embodiment, three conductive strips, whose thicknesses range from 0.05 mm to 1.00 mm respectively includes an electrode working terminal, an electrode lead and an electrode output terminal and all are integrally formed. The sensor strip include an isolating sheet 1601 having a first plane 1602 and a second plane 1603, wherein the second plane 1603 includes a first recess 1604 and a through hole 1605 thereon, as shown in FIG. 16(c), and, the through hole 1605 has another opening on the first plane 1602. Then, a first conductive strip 1606 which is integrally formed is mounted in the first recess 1604 so as to engage with each other, and the first conductive strip 1606 includes a first electrode output terminal 1608 and a first electrode terminal to be a working electrode 1607.

Moreover, the first plane 1602 of the isolating sheet 1601 includes a second recess 1611 and a third recess 1610 thereon for respectively receiving a second conductive strip 1616 and a third conductive strip 1612 mounted therein and engaged with each other. The second conductive strip 1616 which is integrally formed includes a second signal output terminal 1618 and a second electrode terminal to be a counter electrode 1617, and the third conductive strip 1612 which is integrally formed includes a third signal output terminal 1614 and a third electrode terminal to be a reference electrode 1613, wherein the reference electrode 1613 can be modified by a silver chloride modified layer 1615 so as to form an Ag/AgCl reference electrode. An insulating layer 1619 having a C-shaped opening 1620 is covered on the top of two conductive strips 1614 and 1618 except the working electrode 1607 and the electrode output terminal 1608.

Then, a covering layer 1621 having a capillary vent 1622 thereon is covered on the C-shaped opening 1620 for forming a completed capillary adsorbing structure. A chemical reagent 1609 is positioned on the top of the working electrode 1607 for reacting with an analyte in a fluid sample so as to generate an electric signal which is then outputted to the working electrode output terminal 1608 through the electrode 1607. As to number 1623, it represents a fluid inlet.

Figure 17A:
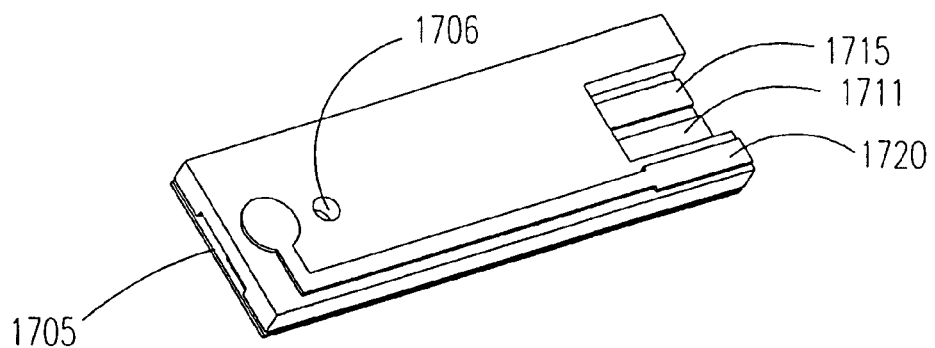
FIGS. 17(a)-(b) respectively, show a reverse view and a decomposed front view of the electrochemical sensor strip having a capillarity channel (which is suitable for micro-liter fluid samples) in another preferred embodiment according to the present invention.
Figure 17B:
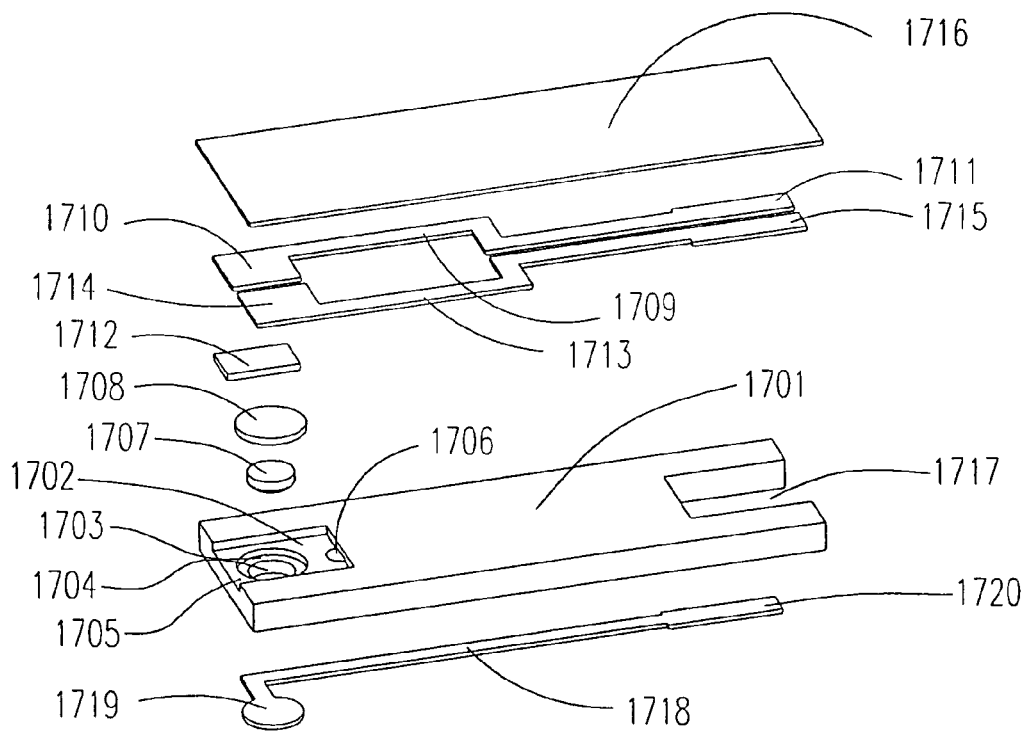
Figure 18A:
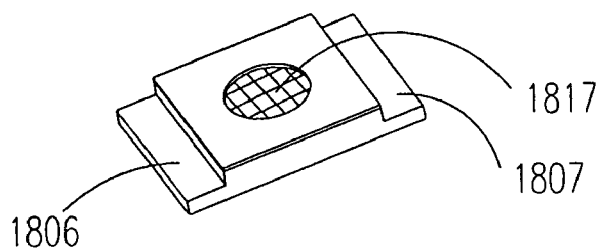
FIGS. 18(a)-(c) respectively, show a front view, a decomposed front view, and a reverse view of the sensor strip in a preferred embodiment according to the present invention.
Figure 18B:
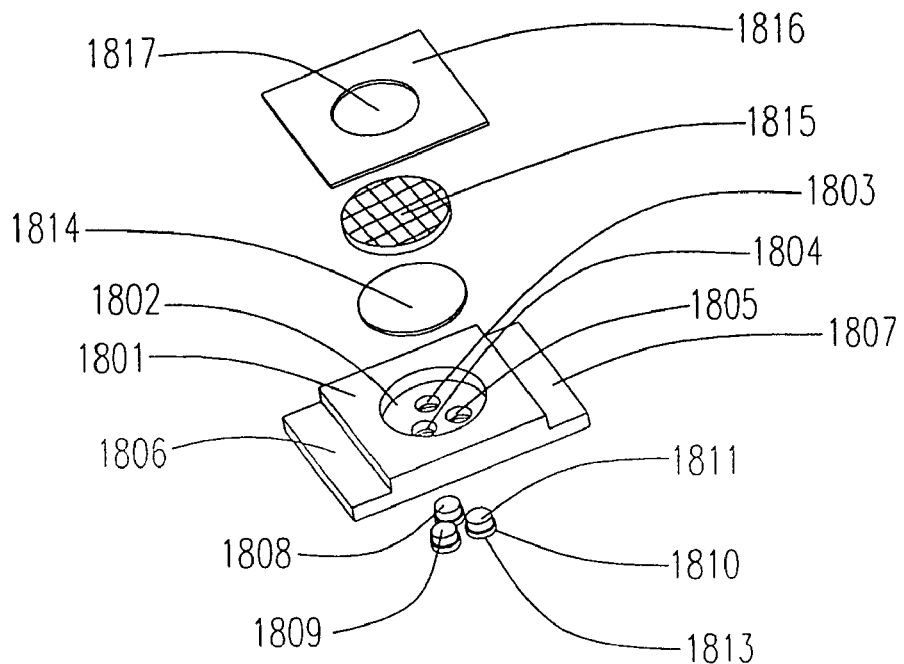
Figure 18C:
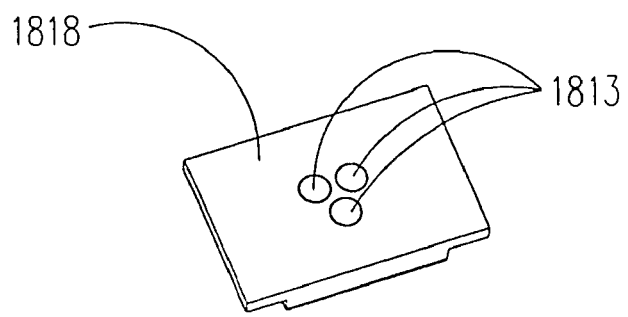
Figure 18D:
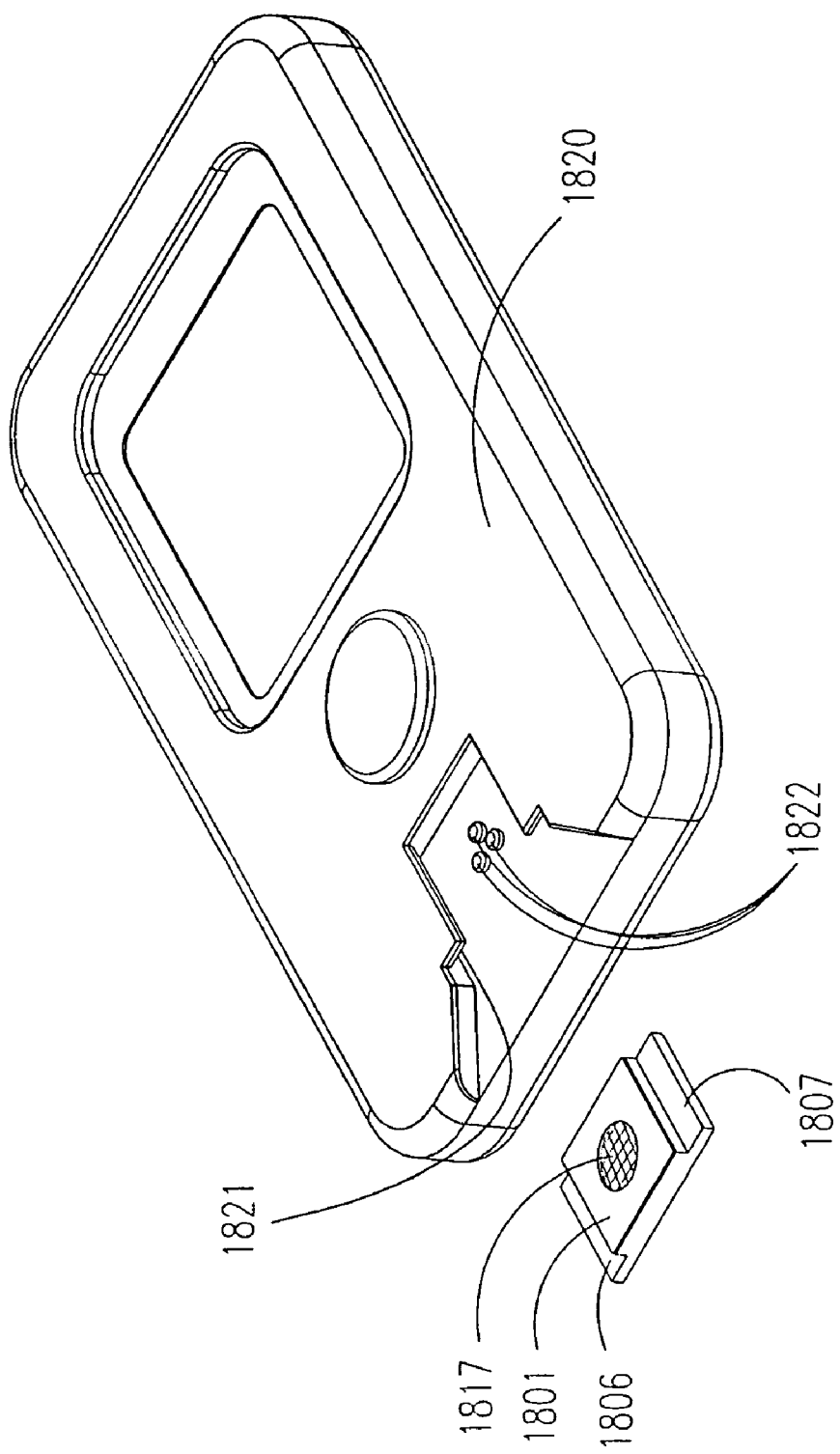
FIG. 18(d) shows a schematic front view of a combination of the sensor strip and a measuring device in a preferred embodiment according to the present invention.

In addition, the embodiment in FIG. 16 can be altered by replacing the counter electrode 1617 and the reference electrode 1613 by traditional printed conductive films printed on the insulating layer 1619, as shown in FIGS. 17(a)-(b). FIGS. 17(a)-(b) illustrate another applying embodiment of a three electrode sensor strip having the capillary channel according to the present invention. The sensor strip includes an isolating sheet 1701 having a fluid measuring recess 1702 thereon, and a chemical reagent placing recess 1703 is positioned at the bottom of the measuring recess 1702 for placing a chemical reagent 1708. Then, a through hole 1704 is positioned under the placing recess 1703 for receiving a first electrode 1707, namely a metal electrode, which is formed by covering a metal film on a conductive raw material. The first electrode 1707 includes a first electrode terminal as a working electrode 1707 and a first electrode connecting surface.

Moreover, a first printed conductive film 1718 is located below the isolating sheet 1701 and includes a connecting terminal 1719 and a signal output terminal 1720, wherein the connecting terminal 1719 is electrically connected to the first electrode connecting surface for outputting a measured signal through the signal output terminal 1720. A capillary vent 1706 is located above the measuring recess 1702 and the number 1705 represents a fluid inlet. A covering layer 1716 is positioned on the fluid measuring recess 1702 for forming a completed capillary adsorbing structure. Furthermore, a second conductive film 1709 and a third conductive film 1713 are printed on the covering layer 1716, wherein the second conductive film 1709 includes a counter electrode output terminal 1711 and a second electrode terminal to be a counter electrode 1710. The third conductive film 1713 includes a reference electrode output terminal 1715 and a third electrode terminal to be a reference electrode 1714, which can be modified by a silver chloride modified layer 1712 so as to form an Ag/AgCl reference electrode.

Besides, a chemical reagent 1708 is positioned on the top of the working electrode 1707 for reacting with an analyte in a fluid sample so as to generate an electric signal which is then outputted to the signal output terminal 1720 through the electrode 1707. As to number 1717, it represents a C-shaped opening.

In this embodiment described above, the counter electrode 1710 and the reference electrode 1714 are printed on the covering layer 1716 for avoiding the working electrode from being polluted when modifying the reference electrode. And, because the isolating sheet 1701 and the covering layer 1716 are separated when modifying, the working electrode will not be contaminated.

Please refer to FIGS. 18(*a*)-(*c*) which illustrate another embodiment for applying a three electrode sensor strip according to the present invention. In this embodiment, the signal output terminals in back of the metal electrodes are directly connected to the input connecting points on a measuring device. The sensor strip includes an isolating sheet 1801 having a fluid measuring recess 1802 and three through holes 1803, 1804 and 1805 are located at the bottom of the measuring recess 1802 for respectively receiving three electrodes 1808, 1809 and 1810 mounted therein and engaged with each other. Each of the electrodes 1808, 1809 and 1810 include a signal output terminal 1813 and an electrode working surface 1811 which is employed to process an electrode action.

A chemical reagent 1814 is positioned on the top of the electrode working surface 1811, a meshed piece 1815 is positioned on the top of the chemical reagent 1814 for protecting the chemical reagent 1814 and filtering an impurity in a fluid sample and a covering layer 1816 having an opening 1817 is covered on the meshed piece 1815 and connected to the isolating sheet 1801, wherein the opening 1817 serves as a fluid sample inlet.

Besides, the isolating sheet 1801 further includes two tenons 1806 and 1807 at two sides thereof so that the sheet 1801 can be slid into two notches 1821 of a measuring device 1820 (as shown in FIG. 18(*d*)) so as to be fixed therein. After the sheet 1801 is slid into the notches 1821, the signal output points 1813 of the sensor strip will be directly connected with the signal connecting points 1822 of the measuring device 1820 so as to complete the signal transmission. Thus, in this embodiment, the printed conductive films on the isolating sheet are no longer needed. As to the number 1818, it represents the backside of the sheet 1801.

If the metal electrode of a disposable sensor strip according to the present invention serves as a working electrode, it can be the first type: "electron-transfer mediator modified working electrode" and the second type: "metal-catalyzed electrode". If the metal electrode according to the present invention serves as the first type electrode, it only needs to employ the noble metal which has no chemical interference and does not need to be limited as a specific kind. In other words, all of gold, platinum, palladium, and rhodium can be employed. This kind of metal electrode according to the present invention utilizes a noble metal film to cover a conductive raw material for forming a metal electrode which is then mounted in a through hole of an isolating sheet. Through this configuration, the used amount of the noble metal used can be reduced and the time for manufacturing the metal electrode also can be shortened. Furthermore, the sensor strip can therefore provide a good performance in the detecting reproducibility because the electrode area thereof can be exactly obtained. If the metal electrode according to the present invention serves as the second type electrode, the material of the working electrode should directly participate in the electrochemical catalysis (namely it doesn't need to add additional electron-transfer mediator therein). Thus, the material should be chemically matched with the chemical reagent and the analyte in the fluid sample. For responding to different chemical reactions, the metal material will not be limited to be the noble metal and can be any kind of metal. For example, a copper electrode can serve as a working electrode for detecting $H_2O_2$. When the material selected is not expensive, the conductive raw material and the metal electrode can be the same for saving the coating procedure of the metal film. Hence, the time for manufacturing the metal electrode still can be shortened, and the sensor strip can therefore provide a good performance in the detecting reproducibility because the electrode area thereof can be exactly obtained. Consequently, through the electrode structure and the manufacturing processes according to the present invention, the disposable sensor strip can significantly reform the defects in the prior arts.

The main principle for designing the structure and manufacturing method in the present invention is how to economize the noble metal material. Therefore, the present invention provides a cheap conductive raw material (such as a copper cylinder having a diameter of 1.0 mm and a thickness of 0.5 mm) for being further electroplated by a noble metal film (such as a rhodium film having a thickness of 0.025-0.075 µm) for forming a noble metal electrode. Then, the electrode is mounted in the through hole of an isolating sheet so as to engage with each other and reveals only an electrode working surface and an electrode connecting surface. The electrode working surface can process an electrode action and a conductive film is further printed to connect to the electrode connecting surface for being a lead and an output terminal of the electrode. In this structure, the noble metal material is only used for the metal film which is further limited to only the electrode area in the through hole. Thus, the amount of the noble metal can be reduced to be minimum. In addition, if millions of raw materials of electrodes are electroplated at a same time, and then put into the through holes of an isolating sheet via a mechanical process, not only the noble metal material but also the manufacturing cost can also be significantly reduced.

The electrode according to the present invention is mounted in the through hole of an isolating sheet, and through the engagement from the isolating sheet, only an electrode working surface and an electrode connecting surface are revealed. Then, a conductive film is further printed to connect to the electrode connecting surface for being a lead and an output terminal of the electrode. Therefore, the electrode working surface is not directly contacted by the conductive film so that the electrode surface is completely independent and decided by the through hole only so as to obtain an extremely accurate electrode area. Because the measured current is proportional to the electrode area, the present invention can greatly improve the reproducibility of the electrochemical sensor strip.

Furthermore, in the present invention, the isolating sheet having the through hole thereon can be formed by an injection-molding method. The same as above, the injection-molding process can also integrally form other structures, such as the fluid sample inlet, the capillary channel recess, the capillary convecting vent, the chemical reagent, placing recess and the protruding spacer. Therefore, the number of the assembling elements, and the assembling error for many of these elements, can be decreased, thereby reducing costs.

In view of the aforesaid, the present invention provides a novel manner which utilizes a metal film to cover on a conductive raw material for reducing the amount of noble metal. Furthermore, the metal electrode is mounted in the through hole of the isolating sheet so that the time for manufacturing the disposable sensor strip according to the present invention can be significantly reduced. Therefore, the present invention is extremely suitable for being used in industrial production.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A disposable electrochemical sensor strip, comprising:
at least a conductive raw material;
a metal film coated on said conductive raw material for forming an electrode which comprises an electrode working surface for processing an electrode action, and a signal output terminal for directly outputting a measured signal; and
an insulation piece having at least a through hole into which the conductive raw material and the metal film are mounted.

2. The sensor strip according to claim 1 further comprising a chemical reagent mounted on said electrode working surface for detecting an analyte contained in a fluid sample through reacting with said analyte so as to generate said measured signal which is then directly outputted through said signal output terminal.

3. The sensor strip according to claim 1 wherein said conductive raw material and said metal film are fully received in said through hole.

4. A disposable electrochemical sensor strip, comprising:
at least a conductive raw material;
a metal film coated on said conductive raw material for forming an electrode for directly outputting a measured signal; and
an insulation piece having at least a through hole into which the conductive raw material and the metal film are mounted.

5. The sensor strip according to claim 4 further comprising a chemical reagent mounted on said electrode working surface for detecting an analyte contained in a fluid sample through reacting with said analyte so as to generate said measured signal which is then outputted through said signal output terminal.

6. The sensor strip according to claim 4 wherein the conductive raw material and the metal film are fully received in the through hole.

7. A disposable electrochemical sensor strip, comprising:
at least a conductive raw material;
a metal film coated on said conductive raw material for forming an electrode which comprises an electrode working surface for processing an electrode action, and a signal output terminal for outputting a measured signal; and
an insulation piece having at least a through hole into which the conductive raw material and the metal film are mounted,
wherein said electrode and said insulation piece are simultaneously formed.

8. The sensor strip according to claim 7, wherein said electrode and said insulation piece are simultaneously formed through a molding device selected from the group consisting of an injection-molding device, a punch press device and a computerized drilling machine.

9. The sensor strip according to claim 7, wherein the conductive raw material and the metal film are fully received in the through hole.

10. A disposable electrochemical sensor strip, comprising:
at least a conductive raw material;
a metal film coated on said conductive raw material for forming an electrode which comprises an electrode working surface for processing an electrode action, and a signal output terminal for outputting a measured signal; and
an insulation piece having at least a through hole into which the conductive raw material and the metal film are mounted,
wherein said sensor strip comprises said insulation piece being the only one insulation piece therein.

11. The sensor strip according to claim 10 further comprising a chemical reagent mounted on said electrode working surface for detecting an analyte contained in a fluid sample through reacting with said analyte so as to generate said measured signal which is then outputted through said signal output terminal.

12. The sensor strip according to claim 10 wherein the conductive raw material and the metal film are fully received in the through hole.

13. A disposable electrochemical sensor strip, comprising:
at least a conductive raw material;
a metal film fully encapsulating said conductive raw material to form an electrode which comprises an electrode working surface for processing an electrode action, and an electrode connecting surface;
an insulation sheet having at least a through hole into which the conductive raw material and the metal film are mounted; and
at least a printed conductive film on said insulation sheet and having a connecting terminal for being electrically connected to said electrode connecting surface, and a signal output terminal for outputting a measuring signal produced by said electrode action,
wherein said electrode forms an electrode area in said through hole whose area is an area of said working surface for processing said electrode action and transmitting said measured signal.

* * * * *

UNITED STATES PATENT AND TRADEMARK OFFICE
CERTIFICATE OF CORRECTION

PATENT NO. : 7,740,746 B2  Page 1 of 1
APPLICATION NO. : 11/415720
DATED : June 22, 2010
INVENTOR(S) : Chun-Mu Huang It is certified that error appears in the above-identified patent and that said Letters Patent is hereby corrected as shown below:

ON THE TITLE PAGE

Delete "(73) Assignee: Delta Electronics, Inc., Taoyuan (TW)"

Signed and Sealed this
Thirty-first Day of May, 2011

David J. Kappos
*Director of the United States Patent and Trademark Office*